(12) United States Patent
Faries, Jr. et al.

(10) Patent No.: US 6,810,881 B2
(45) Date of Patent: Nov. 2, 2004

(54) MEDICAL SOLUTION THERMAL TREATMENT SYSTEM AND METHOD OF CONTROLLING SYSTEM OPERATION IN ACCORDANCE WITH DETECTION OF SOLUTION AND LEAKS IN SURGICAL DRAPE CONTAINERS

(75) Inventors: Durward I. Faries, Jr., Las Vegas, NV (US); Bruce R. Heymann, Vienna, VA (US); Calvin Blankenship, Frostburg, MD (US)

(73) Assignee: O.R. Solutions, Inc., Chantilly, VA (US)

( * ) Notice: Subject to any disclaimer, the term of this patent is extended or adjusted under 35 U.S.C. 154(b) by 184 days.

(21) Appl. No.: 09/983,021

(22) Filed: Oct. 22, 2001

(65) Prior Publication Data

US 2003/0075183 A1 Apr. 24, 2003

(51) Int. Cl.$^7$ .............................................. A61B 19/00
(52) U.S. Cl. .......................................... 128/849; 62/66
(58) Field of Search .................. 128/849–856; 62/66, 68, 340, 342

(56) References Cited

U.S. PATENT DOCUMENTS

| | | |
|---|---|---|
| 2,613,511 A | 10/1952 | Walsh |
| 3,869,596 A | 3/1975 | Howie |
| 3,902,484 A | 9/1975 | Winters |
| 4,270,067 A | 5/1981 | Thomas et al. |
| 4,284,880 A | 8/1981 | Keiser |
| 4,393,659 A | 7/1983 | Keyes et al. |
| 4,458,139 A | 7/1984 | McClean |
| 4,474,016 A | 10/1984 | Winchell |
| 4,522,041 A | 6/1985 | Menzel |
| 4,625,098 A | 11/1986 | Joe |
| 4,782,835 A | 11/1988 | Bernardini |
| 4,828,876 A | 5/1989 | Ohhara et al. |
| 4,869,271 A | 9/1989 | Idris |
| 4,903,710 A | 2/1990 | Jessamine et al. |
| 4,934,152 A | 6/1990 | Templeton |
| 4,967,061 A | 10/1990 | Weber, Jr. et al. |
| 5,040,699 A | 8/1991 | Gangemi |
| 5,042,455 A | 8/1991 | Yue et al. |
| 5,042,981 A | 8/1991 | Gross |
| 5,129,033 A | 7/1992 | Ferrara et al. |
| 5,163,299 A | 11/1992 | Faries, Jr. et al. |
| 5,174,306 A | 12/1992 | Marshall |
| 5,310,524 A | 5/1994 | Campbell et al. |
| 5,331,820 A | 7/1994 | Faries, Jr. et al. |
| 5,333,326 A | 8/1994 | Faries, Jr. et al. |
| 5,345,063 A | 9/1994 | Reusche et al. |
| 5,363,746 A | 11/1994 | Gordon |
| 5,374,813 A | 12/1994 | Shipp |
| 5,383,476 A | 1/1995 | Peimer et al. |

(List continued on next page.)

FOREIGN PATENT DOCUMENTS

JP  06-123532  5/1994

Primary Examiner—Michael A. Brown

(57) ABSTRACT

A drape including a sensing device is disposed over a thermal treatment system having a basin recessed therein to form a drape container or receptacle within the basin for collecting a sterile medium. The thermal treatment system may either heat or congeal the sterile medium. The sensing device is typically disposed through the drape to provide a signal indicating the presence of liquid and/or leaks within the drape container to the system to facilitate control of system operation. In addition, the sensing device may be affixed to a plural basin drape utilized for a multiple basin thermal treatment system. The drape forms a drape receptacle within each basin, while a sensing device is typically disposed within each drape receptacle to detect the presence of liquid and/or a leak within that drape receptacle to facilitate control of system operation in substantially the same manner described above.

68 Claims, 10 Drawing Sheets

U.S. PATENT DOCUMENTS

| | | |
|---|---|---|
| 5,386,835 A | 2/1995 | Elphick et al. |
| 5,396,905 A | 3/1995 | Newman et al. |
| 5,400,267 A | 3/1995 | Denen et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,435,322 A | 7/1995 | Marshall |
| 5,443,082 A | 8/1995 | Mewburn |
| 5,449,892 A | 9/1995 | Yamada |
| 5,457,962 A | 10/1995 | Faries, Jr. et al. |
| 5,463,213 A | 10/1995 | Honda |
| 5,502,980 A | 4/1996 | Faries, Jr. et al. |
| 5,522,095 A | 6/1996 | Faries, Jr. et al. |
| 5,524,478 A | 6/1996 | Joy et al. |
| 5,524,643 A | 6/1996 | Faries, Jr. et al. |
| 5,531,697 A | 7/1996 | Olsen |
| 5,539,185 A | 7/1996 | Polster |
| 5,551,240 A | 9/1996 | Faries, Jr. et al. |
| 5,615,423 A | 4/1997 | Faries, Jr. et al. |
| 5,653,938 A | 8/1997 | Faries, Jr. et al. |
| 5,658,478 A | 8/1997 | Roeschel et al. |
| 5,664,582 A | 9/1997 | Szymaitiz |
| 5,717,188 A | 2/1998 | Vaillancourt |
| 5,800,352 A | 9/1998 | Ferre et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,950,438 A | 9/1999 | Faries, Jr. et al. |
| 6,003,328 A | 12/1999 | Faries, Jr. et al. |
| 6,035,855 A | 3/2000 | Faries, Jr. et al. |
| 6,087,636 A | 7/2000 | Faries, Jr. et al. |
| 6,091,058 A | 7/2000 | Faries, Jr. et al. |
| 6,102,044 A | 8/2000 | Naidyhorski |
| 6,371,121 B1 | 4/2002 | Faries, Jr. et al. |

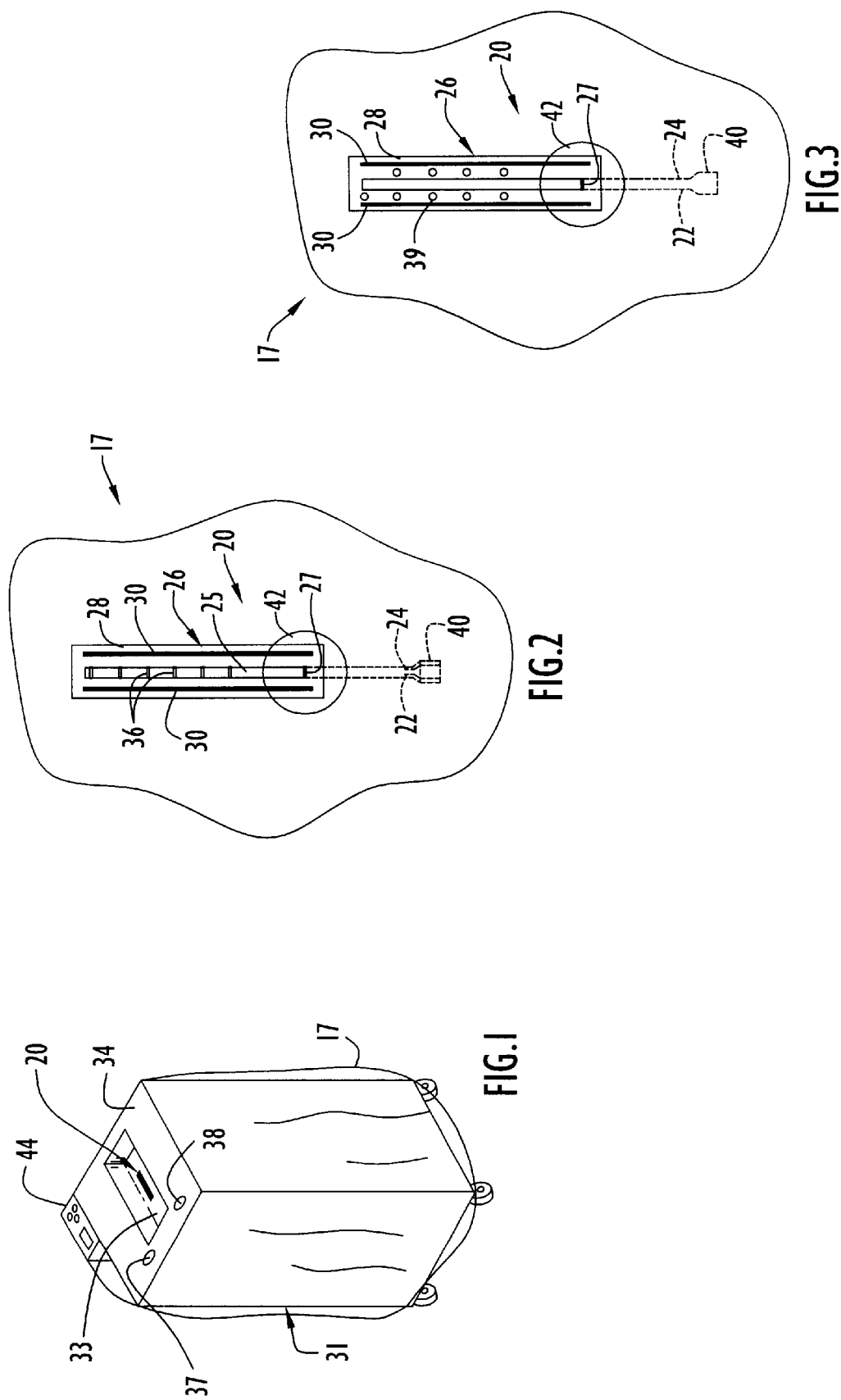

MEDICAL SOLUTION THERMAL TREATMENT SYSTEM AND METHOD OF CONTROLLING SYSTEM OPERATION IN ACCORDANCE WITH DETECTION OF SOLUTION AND LEAKS IN SURGICAL DRAPE CONTAINERS

BACKGROUND OF THE INVENTION

1. Technical Field

The present invention pertains to improvements in methods and apparatus for thermally treating a sterile surgical liquid. In particular, the present invention pertains to a thermal treatment system employing a corresponding surgical drape to contain a sterile surgical solution therein, wherein the presence of solution and/or leaks within the drape container is detected to control system operation. The present invention is an improvement of the methods and apparatus disclosed in U.S. Pat. Nos. 4,393,659 (Keyes et al), 4,934,152 (Templeton), 5,163,299 (Faries, Jr. et al), 5,331,820 (Faries, Jr. et al), 5,333,326 (Faries, Jr. et al), 5,400,616 (Faries, Jr. et al), 5,402,644 (Faries, Jr. et al), 5,429,801 (Faries Jr. et al), 5,457,962 (Faries, Jr. et al), 5,502,980 (Faries, Jr. et al), 5,522,095 (Faries, Jr. et al), 5,524,643 (Faries, Jr. et al), 5,551,240 (Faries, Jr. et al), 5,615,423 (Faries, Jr. et al), 5,653,938 (Faries, Jr. et al), 5,809,788 (Faries, Jr. et al), 5,816,252 (Faries, Jr. et al), 5,857,467 (Faries, Jr. et al), 5,862,672 (Faries, Jr. et al), 5,879,621 (Faries, Jr. et al), 5,950,438 (Faries, Jr. et al), 6,003,328 (Faries, Jr. et al), 6,035,855 (Faries, Jr. et al), 6,087,636 (Faries, Jr. et al), 6,091,058 (Faries, Jr. et al), 6,255,627 (Faries, Jr. et al) and copending U.S. patent application Ser. No. 09/572,903, filed May 17, 2000 and entitled "Remote Controlled Thermal Treatment System and Method for Controlling the System Remotely to Thermally Treat Sterile Surgical Liquid". The disclosures in the above-mentioned patents and copending patent application are incorporated herein by reference in their entireties.

2. Discussion of the Related Art

The above-referenced Keyes et al patent (U.S. Pat. No. 4,393,659) discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent (U.S. Pat. No. 4,934,152), the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent (U.S. Pat. No. 4,934,152) discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al patent (U.S. Pat. No. 5,163,299) notes that scraping congealed liquid from the drape is undesirable in view of the potential for damage to the drape, resulting in a compromise of sterile conditions. As a solution to the problem, the Faries, Jr. et al patent (U.S. Pat. No. 5,163,299) proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel. Accordingly, several of the Faries, Jr. et al patents (e.g., U.S. Pat. Nos. 5,331,820; 5,400,616; 5,457,962; 5,502,980; 5,653,938; 5,809,788; 5,857,467; 5,950,438; 6,003,328; and 6,035,855) resolve the problem of manual drape manipulation by disclosing various techniques and/or dislodgment mechanisms to automatically remove the congealed liquid adhering to the drape without endangering the integrity of the drape.

The Templeton patent (U.S. Pat. No. 4,934,152) further discloses an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both warmed sterile liquid and sterile surgical slush. Accordingly, several of the Faries, Jr. et al patents (e.g., U.S. Pat. Nos. 5,333,326; 5,429,801; 5,522,095; 5,524,643; 5,615,423; 5,653,938; 5,816,252; 5,862,672; 5,857,467; 5,879,621; 6,091,058; and 6,255,627) disclose a manner in which to simultaneously provide both surgical slush and warmed surgical liquid during a surgical procedure by utilizing a machine having plural basins with each basin either producing surgical slush or heating a sterile liquid. This machine typically utilizes a single surgical drape that forms a drape receptacle within each basin to collect sterile slush and heated sterile liquid produced by the machine in the respective basins.

In addition, several of the drapes and thermal treatment systems disclosed in the above-mentioned patents and copending application include specialized features to enhance various aspects of thermal treatment system operation. For example, some of the specialized features may include: bladder drapes (e.g., as disclosed in U.S. Pat. Nos. 5,809,788; 5,950,438; and 6,003,328); drapes having plates or disks (e.g., as disclosed in U.S. Pat. Nos. 5,457,962 and 5,502,980); reinforced drapes (e.g., as disclosed in U.S. Pat. No. 5,857,467); drape indicators and corresponding thermal treatment system detection devices to ensure sterility by enabling system operation in response to detecting a sterile drape placed on the system (e.g., as disclosed in U.S. Pat. Nos. 5,653,938 and 5,879,621); drapes having indicia to direct placement of the drapes on thermal treatment systems (e.g., as disclosed in U.S. Pat. No. 5,615,423); surgical drapes constructed of materials having a coefficient of friction in a particular range and/or drapes including attachment mechanisms such that a drape may withstand being drawn under a dislodgment mechanism (e.g., as disclosed in U.S. Pat. No. 6,035,855); a stand to elevate objects within a heated basin above the basin floor (e.g., as disclosed in U.S. Pat. No. 6,087,636) and/or a heater configured to cover a portion of the basin (e.g., as disclosed in U.S. Pat. Nos. 6,091,058 and 6,255,627) to prevent the drape from overheating and puncturing when objects are placed within the basin; and remote control of a thermal treatment system (e.g., as disclosed in U.S. patent application Ser. No. 09/572,903).

However, when insignificant amounts of liquid are present within a thermal treatment system basin, the system heating and cooling mechanisms operate with minimal thermal resistance, thereby enabling the mechanisms to become damaged. Further, the drapes employed by the system may be damaged by being disposed proximate the heating or cooling mechanism without having the liquid to absorb the thermal energy. Since only sterile drapes are to be used during surgical procedures, a leak in a surgical drape compromises sterility and contaminates the entire surgical procedure, thereby increasing the risk of injury to a patient.

The related art has attempted to overcome this problem by employing sensing devices with surgical drapes. For example, U.S. Pat. No. 5,524,643 (Faries, Jr. et al) discloses a surgical drape combined with a sensor, preferably attached to the drape, to detect the presence of liquid within a drape container conforming to a heating/cooling thermal treatment system basin. An alternative embodiment employs sensors at opposite surfaces of the drape to measure conductance and, thereby, leakage through the drape. A microprocessor of each embodiment receives a signal representing, for example, an electrical conductance measurement and determines the presence of liquid and/or a leak. If liquid is not present or a leak is determined to exist, the microprocessor disables a temperature controller for the basin to prevent damage to the drape and heating and cooling mechanisms.

U.S. Pat. No. 5,816,252 (Faries, Jr. et al) discloses a drape for use with a system for thermally treating a sterile medium. The drape includes liquid sensitive material that changes color upon contact with liquid to indicate the presence of a leak. The liquid sensitive material may be placed between the drape and a receiving basin or affixed to the drape in the form of indicia symbolically directing placement of the drape over the system. The system may include a single basin and be of the type that either thermally cools or heats the sterile medium, or the system may include a plurality of basins with each basin either thermally cooling or heating the sterile medium. The liquid sensitive material detects leaks within the drape while assisting the operator in properly aligning and placing the drape over the system.

U.S. Pat. No. 6,102,044 (Naidyhorski) discloses an electrode carrying surgical drape including a polymeric film having opposing surfaces and an electrode receiving aperture therethrough. An electrode is disposed through the aperture, while patches sealingly affix electrode portions to each of the opposing surfaces of the polymeric film in the vicinity of the aperture to form a reinforced laminated structure capable of maintaining the sterility of an established sterile field.

The above-described systems can stand some improvement. In particular, the Faries, Jr. et al sensor drape (U.S. Pat. No. 5,524,643) employs a plug connector disposed through the drape to facilitate connections between the drape sensor and the thermal treatment system, thereby complicating the process of effectively sealing the drape to prevent contamination of the sterile field. Further, the drape is required to be placed on the system with the plug aligned with a corresponding plug receptacle for system operation, thereby restricting the manners in which the drape maybe positioned on the system to form the drape container. The Faries, Jr. et al system employing liquid sensitive material with a drape (U.S. Pat. No. 5,816,252) indicates the presence of a leak within the drape container. However, this system relies on operating room personnel to respond to the leak indication and perform appropriate actions with respect to system operation. Thus, the system may continually operate in the presence of a drape container leak until personnel notice and respond to the leak indication, thereby increasing the risk of contamination of a surgical procedure and damage to the system heating or cooling mechanism when a drape leak occurs. The Naidyhorski drape utilizes a plurality of patches to sealingly affix the electrode to the drape, thereby increasing system materials, complexity and costs. Moreover, the Naidyhorski electrode primarily serves as a conduit or path through the drape and typically requires additional components to perform sensing functions, thereby increasing costs and complexity of employing that drape with sensing functions.

OBJECTS AND SUMMARY OF THE INVENTION

Accordingly, it is an object of the present invention to detect the presence of solution and/or a leak within a drape container disposed in a thermal treatment system basin and control system operation in accordance with detected drape container conditions.

It is another object of the present invention to dispose a conductor or other object through a sterile surgical drape while maintaining the sterile field.

Yet another object of the present invention is to employ a surgical drape including solution and/or leak sensors with a thermal treatment system including circuitry that interfaces the drape to control system operation in accordance with drape conditions detected by the sensors and circuitry.

The aforesaid objects may be achieved individually and/or in combination, and it is not intended that the present invention be construed as requiring two or more of the objects to be combined unless expressly required by the claims attached hereto.

According to the present invention, a drape including a sensing device is disposed over a top surface of a thermal treatment system having a basin recessed therein. A portion of the drape is pushed down into, and conforms to, the basin to form a drape container or receptacle within the basin for collecting a sterile medium. The thermal treatment system may be of the type that either heats or congeals the sterile medium to respectively produce a warm sterile liquid or sterile slush within the basin. The sensing device is typically disposed through the drape to provide a signal indicating the presence of liquid and/or leaks within the drape container to the system to facilitate control of system operation. In addition, the sensing device may be affixed to a drape utilized for a multiple basin thermal treatment system wherein each basin may either heat or congeal the sterile medium as described above. The multiple basin drape forms a drape receptacle within each basin, while a sensing device is typically disposed within each drape receptacle to detect the presence of liquid and/or a leak within that drape receptacle and provide a signal to the system to facilitate control of system operation in substantially the same manner described above.

The above and further objects, features and advantages of the present invention will become apparent upon consideration of the following detailed description of specific embodiments thereof, particularly when taken in conjunction with the accompanying drawings, wherein like reference numerals in the various figures are utilized to designate like components.

BRIEF DESCRIPTION OF THE DRAWINGS

FIG. 1 is a view in perspective of a surgical drape including a sensing device and disposed over a thermal treatment system according to the present invention.

FIG. 2 is a view in perspective of the surgical drape of FIG. 1 according to the present invention.

FIG. 3 is a view in perspective of an alternative surgical drape including a sensing device according to the present invention.

DETAILED DESCRIPTION OF THE PREFERRED EMBODIMENTS

Figure 4:
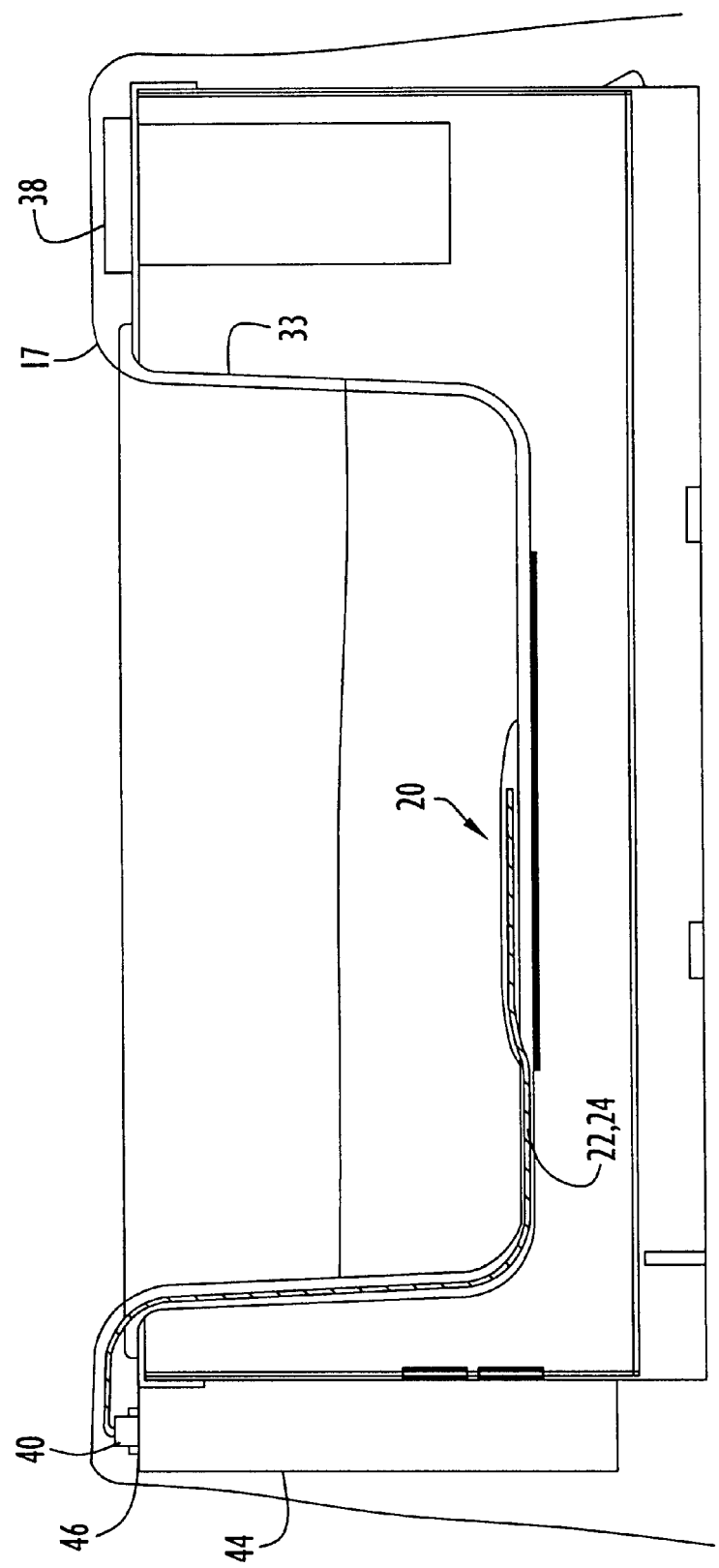
FIG. 4 is a view in elevation and partial section of a basin portion of the thermal treatment system of FIG. 1 with the drape placed thereon.

A thermal treatment system and corresponding drape according to the present invention for heating a sterile medium (e.g., solution or liquid) and for detecting the presence of the medium and leaks within a drape container is illustrated in FIG. 1. Specifically, the system includes a cabinet or housing 31, a wiring housing 44 attached to the cabinet and a warming basin 33 recessed into a cabinet top surface 34. Basin 33 may be of any shape, however, by way of example only, the basin is illustrated as being substantially rectangular. A heater power switch 37 and a temperature controller/indicator 38 are provided on top surface 34 toward the cabinet front wall with the warming basin residing between the power switch and controller. Wiring housing 44 is attached to the cabinet side wall that is closest to heater power switch 37 and facilitates system connections as described below. A heater 70 (FIG. 7) is disposed on the underside of the basin to heat the basin and the sterile medium contained therein. The heater is controlled by controller 38 in accordance with an entered desired temperature and temperatures measured by a temperature sensor 72 (FIG. 7) as described below. Heater 70 is typically implemented by a conventional etched foil silicon rubber heating pad and is attached to the basin underside via a pressure sensitive or other type of adhesive. The heater may alternatively be of any quantity (e.g., at least one), shape or size, and may include any configuration (e.g., strips, bars, segments, etc.) that covers the entirety or any portion of the basin. In addition, the heater may be implemented by any conventional or other type of heater or heating element (e.g., heating coils, etc.) that may be disposed on the basin at any suitable locations.

Temperature sensor 72 is preferably implemented by a conventional resistive temperature device (RTD) (e.g., a 1,000 Ohm RTD). However, the sensor may be implemented by any conventional or other type of temperature sensor, and may be disposed at any suitable location on the basin or within the cabinet. It is to be understood that the thermal treatment system described above may have various configurations. For example, the thermal treatment system may be configured to cool and/or congeal the medium to produce cooled liquid or surgical slush. In this instance, the heater may be replaced by refrigeration devices that are controlled in substantially the same manner described below in response to detection of solution and leaks within the drape container. Further, the thermal treatment system may include a plurality of basins warming and/or cooling a sterile medium as described below. Examples of cooling and/or plural basin systems are disclosed in several of the above-mentioned Faries, Jr. et al. patents (e.g., U.S. Pat. Nos. 5,333,326; 5,429,801; 5,522,095; 5,524,643; 5,615,423; 5,653,938; 5,816,252; 5,862,672; 5,857,467; 5,879,621; 6,091,058; and 6,255,627).

A sterile drape 17, preferably transparent, is typically disposed over the top and sides of cabinet 31 and made to conform to the side wall and bottom of basin 33. Power switch 37 and controller 38 are disposed on top surface 34 of system cabinet 31 and are adjustable manually through drape 17. The portion of drape 17 disposed in basin 33 serves as a sterile container or receptacle for sterile liquid placed therein to be heated. Typical sterile liquid treated by the thermal treatment system is a 0.80% to 0.95% sodium chloride solution (i.e., saline). Drape 17 is made from a material that is impervious to the sterile liquid and sufficiently soft and flexible to conform to a basin wall. The thickness of the drape is preferably minimized to render thermal transfer therethrough most efficient, yet the thickness is sufficient to resist tearing and puncturing during normal use. The drape may be made of materials commonly used in hospitals for surgical drapes and has a thickness, by way of example only, of approximately five mils. However, the drape may have a thickness in the approximate range of three through ten mils. Drape 17 may also be made of polyurethane film as disclosed for the drape in U.S. Pat. No. 4,934,152 (Templeton). The drape may further include a preformed container portion contoured to match the contour of a basin. The preformed container portion is typically thicker than the remaining portions of the drape described above in order to resist puncture and enable the container portion to maintain the shape of the basin. By way of example only, the container portion may be made of a heavy gauge polyethylene/ionomer resin blend having a thickness of approximately ten through sixteen mils. The percentage of ionomer resin in the blend is in the approximate range of forty to seventy percent. The drape is designed to be disposable after a single use and is provided presterilized and prepackaged in a manner to preserve its sterile state during storage.

The drape is typically positioned over the thermal treatment system with a portion of the drape disposed in a basin to form a drape receptacle as described above. The drape forms a sterile field above the basin to maintain sterility of the sterile medium. However, a puncture, tear or other opening in the drape disrupts the sterile field and may contaminate the sterile liquid, thereby risking injury to a patient. Further, the thermal treatment system may damage the drape (e.g., via the heating or refrigeration device) in the event that liquid is not present within the drape container.

In order to detect the presence of liquid and/or leaks within the drape container to maintain drape integrity and sterility of the sterile medium, drape 17 includes a sensing device as illustrated in FIG. 2. Specifically, drape 17 is substantially rectangular and includes a sensing device 20 to detect the presence of liquid and leaks within a drape container. Sensing device 20 is in the form of a pair of electrodes 22, 24 that are affixed to a generally rectangular strip 25 disposed on an intermediate portion of the drape sterile surface. The electrodes are disposed on the electrode strip toward respective strip longer dimensioned edges and extend substantially in parallel. The electrode strip is enclosed within a pouch 26 to secure the electrodes to the drape and to protect the electrodes from sharp objects that may be disposed within the basin. In addition, the pouch assists to prevent grounding of the electrodes or formation of a current flow path therebetween due to placement of conductive objects (e.g., instruments, stainless steel pitchers, etc.) in the basin that may produce erroneous detections as described below. The pouch is formed from a substantially rectangular segment or flap 28 that is attached (e.g., welded) to the drape sterile surface and sealed by seams 30, each formed toward and extending along a respective flap longer dimensioned edge. The distal ends of the electrodes are attached to a plug or connector 40 that interfaces detection circuitry within the thermal treatment system as described below. The plug includes electrode traces disposed on a plug top surface. The distal portions of strip 25 and electrodes 22, 24 pass through the drape from the sterile to the non-sterile drape sides via an opening or slit 27 defined in the drape at a location slightly offset from a drape central portion. A substantially circular segment or patch 42 is attached to the sterile drape surface to seal opening 27. The patch basically encompasses opening 27 and effectively seals that opening to prevent escape of liquid from, and maintain sterility of, the drape container. Flap 28 and patch 42 are preferably constructed of drape materials, however, the flap and patch maybe constructed of any suitable materials, may be of any shape or size, and may be disposed on the drape at any suitable locations via any conventional or other techniques.

Sensing device 20 detects the presence of liquid and leaks within the drape container in response to placement of drape 17 over the thermal treatment system. In particular, current flow between the electrodes is initiated in response to the electrodes contacting liquid. Further, the presence of a leak within the drape container enables current to flow between the electrodes and ground (e.g., the basin beneath the drape). The current flow from each of these conditions causes a respective change in voltage that is detected by detection circuitry within the thermal treatment system as described below. The magnitude of the voltage change is utilized by the detection circuitry to detect the presence of solution and/or leaks within the drape container and to control system operation in accordance with the detected conditions. Wiring housing 44 (FIG. 1) receives signals from the electrodes and includes wiring to transfer signals between that housing and the detection circuitry. The housing further includes indicators in the form of light emitting diodes to indicate drape container conditions. The detection circuitry determines the drape container conditions based on the electrode signals and controls system operation accordingly. In addition, the detection circuitry selectively illuminates the diodes to indicate the particular determined drape container conditions as described below.

In order to enable the liquid in the drape container to contact the electrodes and facilitate current flow between those electrodes, flap 28 includes a series of slots 36. The slots are defined in the flap between seams 30 and are spaced from each other in a direction of the flap longer dimension. The slots are generally rectangular and extend substantially perpendicular to electrodes 22, 24. Each slot includes a longer dimension substantially similar to the width of strip 25 and encompasses portions of each electrode 22, 24 to facilitate enhanced exposure of the electrodes to liquid within the drape container. Alternatively, flap 28 may include a series of substantially circular openings 39 defined therein to permit contact between the liquid and electrodes as illustrated in FIG. 3. Flap 28 may include any quantity of slots or openings of any shape or size and disposed at any locations in any desired fashion to facilitate contact between the electrodes and liquid within the drape container.

Referring to FIG. 4, drape 17 is disposed over the thermal treatment system and within basin 33 to conform to the basin and form a drape container as described above. Electrodes 22, 24 are disposed on the sterile surface of the drape and pass through the drape to the non-sterile drape surface adjacent the basin bottom. The electrodes extend along basin walls beneath the drape to wiring housing 44 attached to cabinet 31. The wiring housing includes a receptacle 46 for receiving connector 40, thereby connecting the drape to detection circuitry disposed within the cabinet as described below. The wiring housing and/or receptacle may alternatively be disposed at any location on cabinet 31 (e.g., top surface, side walls, cabinet interior, etc.). The electrodes provide signals to the detection circuitry to facilitate detection of liquid and/or leaks within the drape container.

Figure 5:
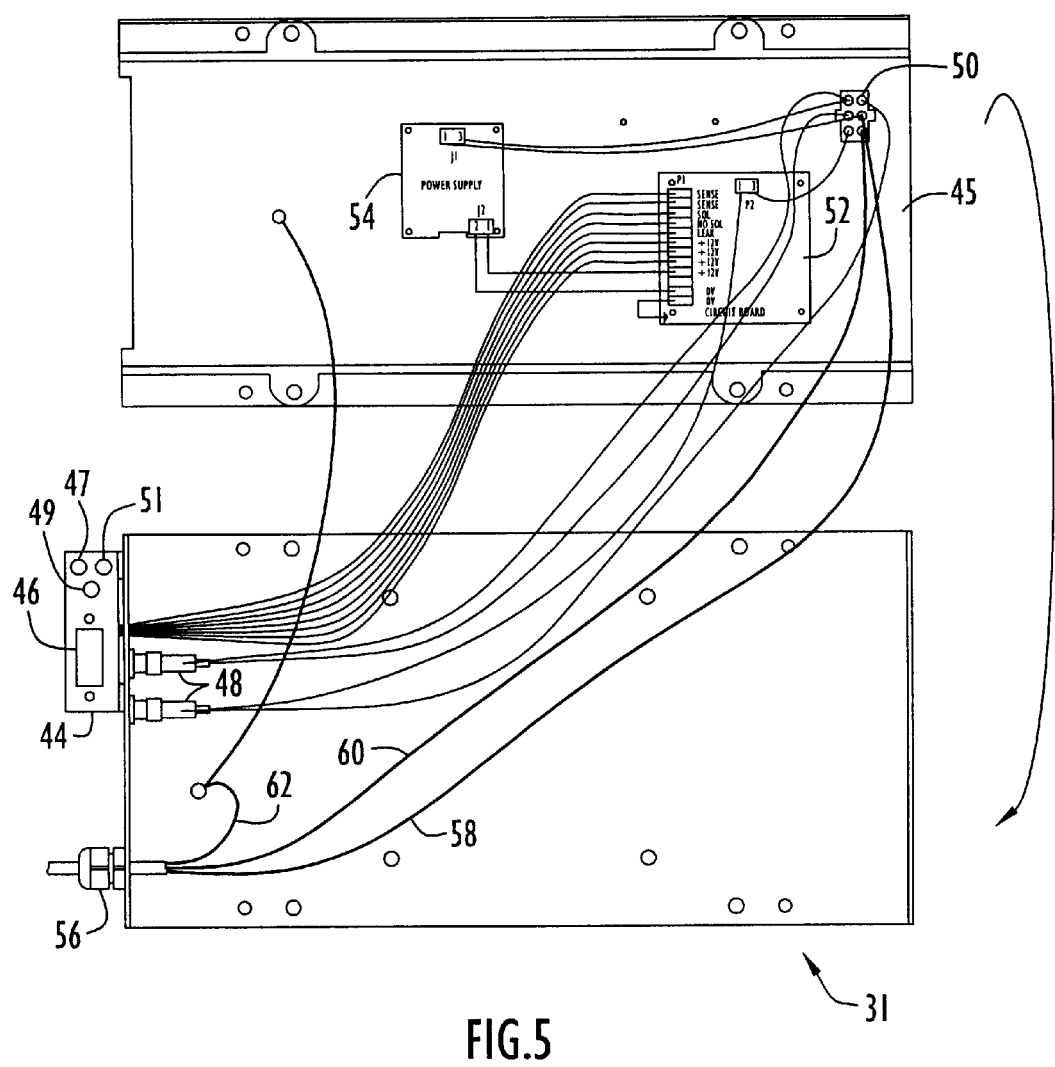
FIG. 5 is an exploded top view of the thermal treatment system of FIG. 1 illustrating system electrical connections.

The manner in which the detection circuitry and associated connections are facilitated within the cabinet is illustrated, by way of example only, in FIG. 5. Specifically, the upper portion of cabinet 31 includes the basin (not shown) and corresponding wiring. Wiring housing 44 is mounted on a cabinet side wall toward the cabinet rear portion, while a power cord 56 is disposed on that side wall toward a cabinet front portion. Wiring housing 44 includes receptacle 46 and light-emitting diodes 47, 49, 51 that indicate drape container conditions. By way of example only, the wiring housing includes: green diode 47 to indicate operation of the system (e.g., solution present without a drape container leak); yellow diode 49 to indicate the absence of solution and leaks within the drape container; and red diode 51 to indicate the presence of a leak within the drape container. The detection circuitry basically prevents system operation (e.g., disables controller 38) in response to a leak or the absence of liquid within the drape container, or in response to the absence of a connection between the drape and the thermal treatment system. The wiring housing receives connector 40 within receptacle 46 and facilitates connections via appropriate wiring between the receptacle, diodes and a circuit board 52 of the detection circuitry containing a condition circuit as described below. The wiring extends through housing 44 and the adjacent cabinet side wall to circuit board 52. Fuses 48 are disposed in the cabinet side wall adjacent wiring housing 44. The fuses protect the system circuitry from power surges and/or spikes that may cause damage to the system.

A generally rectangular base or plate 45 is disposed within the cabinet upper portion above fuses 48. The top surface of the plate supports basin 33, while the underside of the plate includes circuit board 52, a corresponding power supply 54 and a wiring harness connector 50. The circuit board is connected to power supply 54, a corresponding fuse 48, diodes 47, 49, 51 and receptacle 46 via the wiring. Power conductors 58, 60 are connected to power cord 56 and are associated with a ground 62 connected or grounded to the cabinet upper portion and plate. Connector 50 is connected to power conductors 58, 60, fuses 48, power supply 54 and circuit board 52 to establish appropriate connections between the components.

Figure 6:
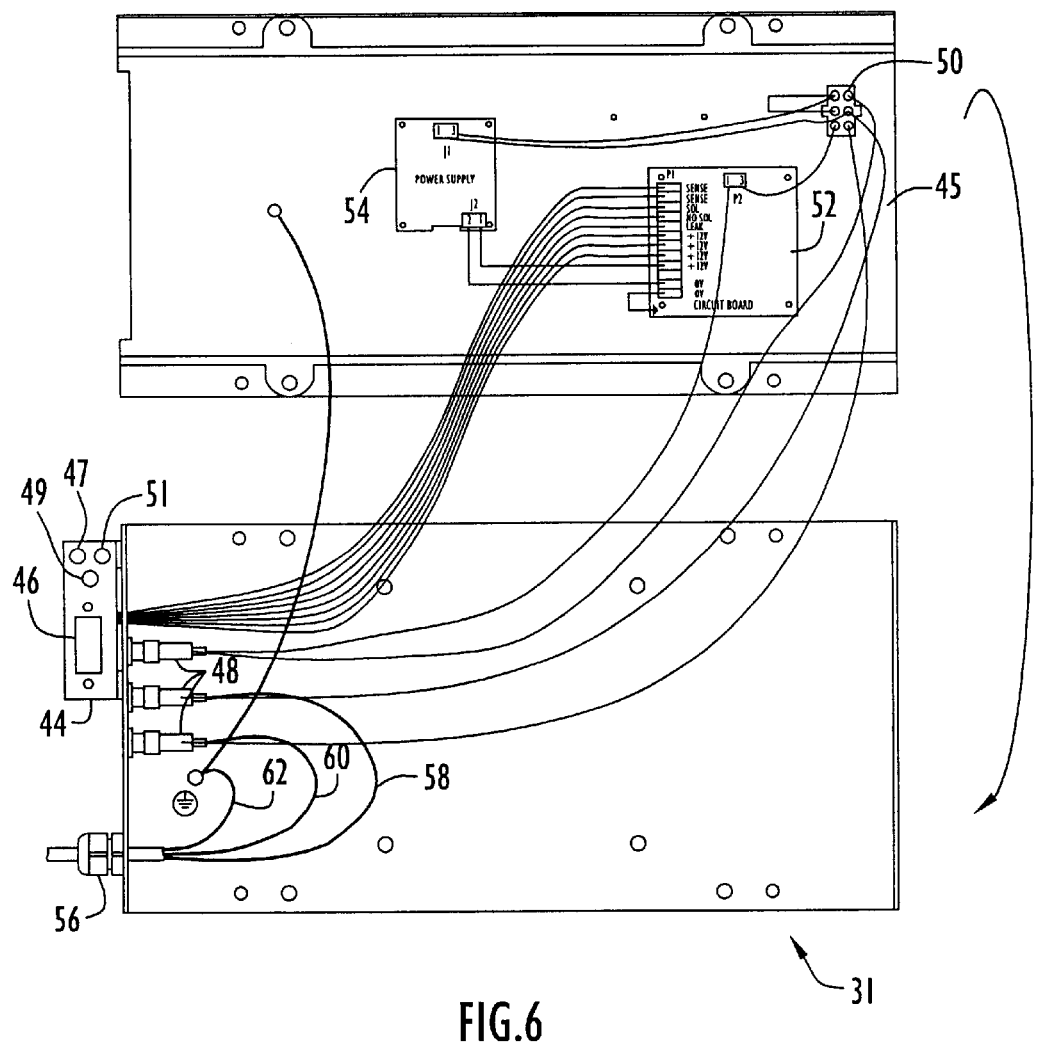
FIG. 6 is an exploded top view of the thermal treatment system of FIG. 1 illustrating an alternative arrangement for system electrical connections.

Alternatively, three fuses 48 may be employed in the system wiring as illustrated, by way of example only, in FIG. 6. This arrangement is substantially similar to the arrangement described above for FIG. 5 except that the alternative arrangement includes an additional fuse 48, and power conductors 58, 60 are each directly connected to a corresponding fuse. Connector 50 is connected to the fuses, power supply and circuit board to establish appropriate connections, while the circuit board is further connected to power supply 54, a corresponding fuse 48, diodes 47, 49, 51 and receptacle 46 via wiring as described above.

Figure 7:
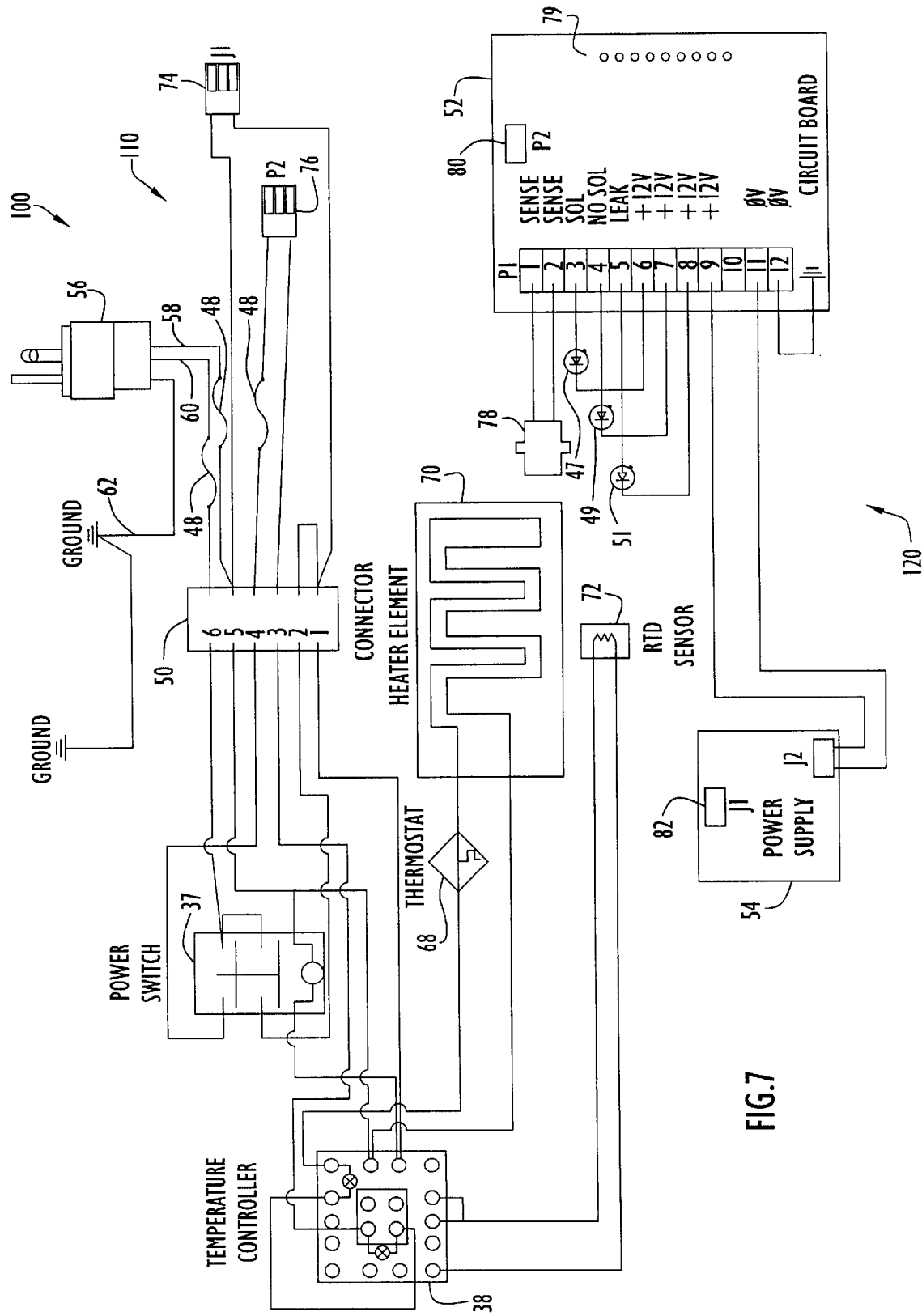
FIG. 7 is an electrical schematic diagram of control circuitry of the thermal treatment system of FIG. 1.

An exemplary control circuit for controlling system operation is illustrated in FIG. 7. The control circuit is illustrated with respect to the wiring arrangement of FIG. 6, however, any suitable wiring arrangement may be employed. Specifically, control circuit 100 includes heat control circuitry 110 and detection circuitry 120. Heat control circuitry 110 includes connector 50, power switch 37, temperature controller 38, heater 70 and temperature sensor 72. Power plug or cord 56, preferably a hospital grade plug (e.g., 115V AC), is connected to a hospital outlet receptacle and to power conductors 58, 60 and ground 62. Fuses 48 are disposed in series with the respective power conductors between connector 50 and plug 56 to protect the system circuitry from damage as described above. Connector 50 is further connected to power switch 37, controller 38 and connector plugs 74, 76 that interface detection circuitry 120 as described below. An additional fuse 48 is disposed between plug 76 and connector 50 to protect the circuitry from power surges. The connector facilitates appropriate connections between the circuitry components as described above.

Power switch 37 enables power to the system and is connected to controller 38. The controller is further connected to heater 70 and temperature sensor 72 to control the heater in response to a desired or set point temperature entered by a user and the temperature measured by the temperature sensor. In particular, controller 38 is typically implemented by a conventional temperature controller and controls power to the heater based on a comparison of the temperature measured by temperature sensor 72 and the set point temperature entered by the user. When the measured temperature exceeds the set point temperature, controller 38 disables or reduces power to the heater. Conversely, when the measured temperature is below the set point temperature, controller 38 enables or increases power to the heater. By way of example only, controller 38 may be implemented by a 16A Series or a 1600 Series Temperature/Process controls available from Love Controls, a Division of Dwyer Instruments, Incorporated. A thermostat 68 is disposed between the controller and heater and basically disables current to heater 70 in response to a temperature measurement exceeding a temperature threshold. In other words, the thermostat disables the heater in response to detection of excessive heater temperatures. The thermostat may be implemented by any conventional switching type or limiting devices, such as a high limit thermostat, and may be disposed at any suitable location within the cabinet.

Controller 38 further controls heater 70 in response to signals received from detection circuitry 120. The detection circuitry detects the presence of solution and leaks within the drape container and provides appropriate signals to heat control circuitry 110 via plug 76. The heat control circuitry disables the heater in response to the absence of solution within the drape container and/or a drape container leak as indicated by the detection circuitry signals.

The detection circuitry includes circuit board 52 including a condition circuit 53 (FIG. 8), power supply 54 and diodes 47, 49, 51 indicating the drape container conditions. The circuit board includes a series of pins or terminals 1–12 to facilitate connections, a plurality of indicator lights 79 and a plug receptacle 80 for receiving plug 76 of heat control circuitry 110. By way of example only, pins 1 and 2 are connected to the wiring housing receptacle or connector 46 to receive electrode signals, while pins 9 and 11 are connected to the positive and reference terminals of power supply 54, respectively. Pins 6–8 are connected to pin 9 and provide a voltage (e.g, +12V DC) to the condition circuit, while pin 12 is connected to pin 11 and provides a ground. Green diode 47 is connected between pins 3 and 6 and is illuminated in response to detection of solution within the drape container without a leak, while yellow diode 49 is connected between pins 4 and 7 and is illuminated in response to detection of the absence of solution and a leak within the drape container. Red diode 51 is connected between pins 5 and 8 and is illuminated in response to detection of a leak within the drape container. Pin 10 is basically inoperable and utilized to facilitate compatible connections with the board. Power supply 54 includes a plug receptacle 82 to receive plug 74 of heat control circuitry 110, thereby providing power signals from power plug 56 to the power supply.

Figure 8:
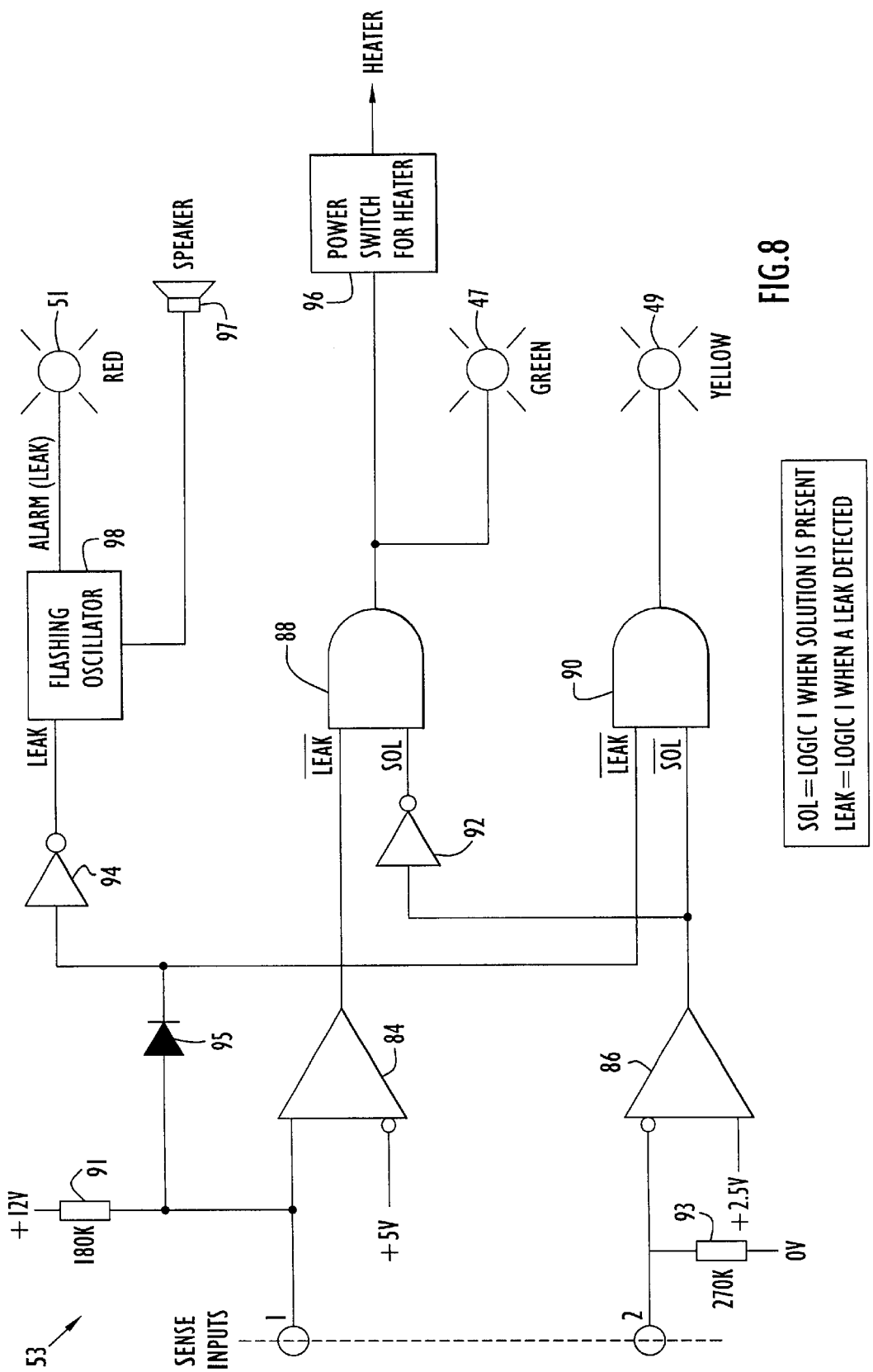
FIG. 8 is a schematic block diagram of a condition circuit for determining the presence of liquid and/or leaks within a drape container.
Figure 9A:
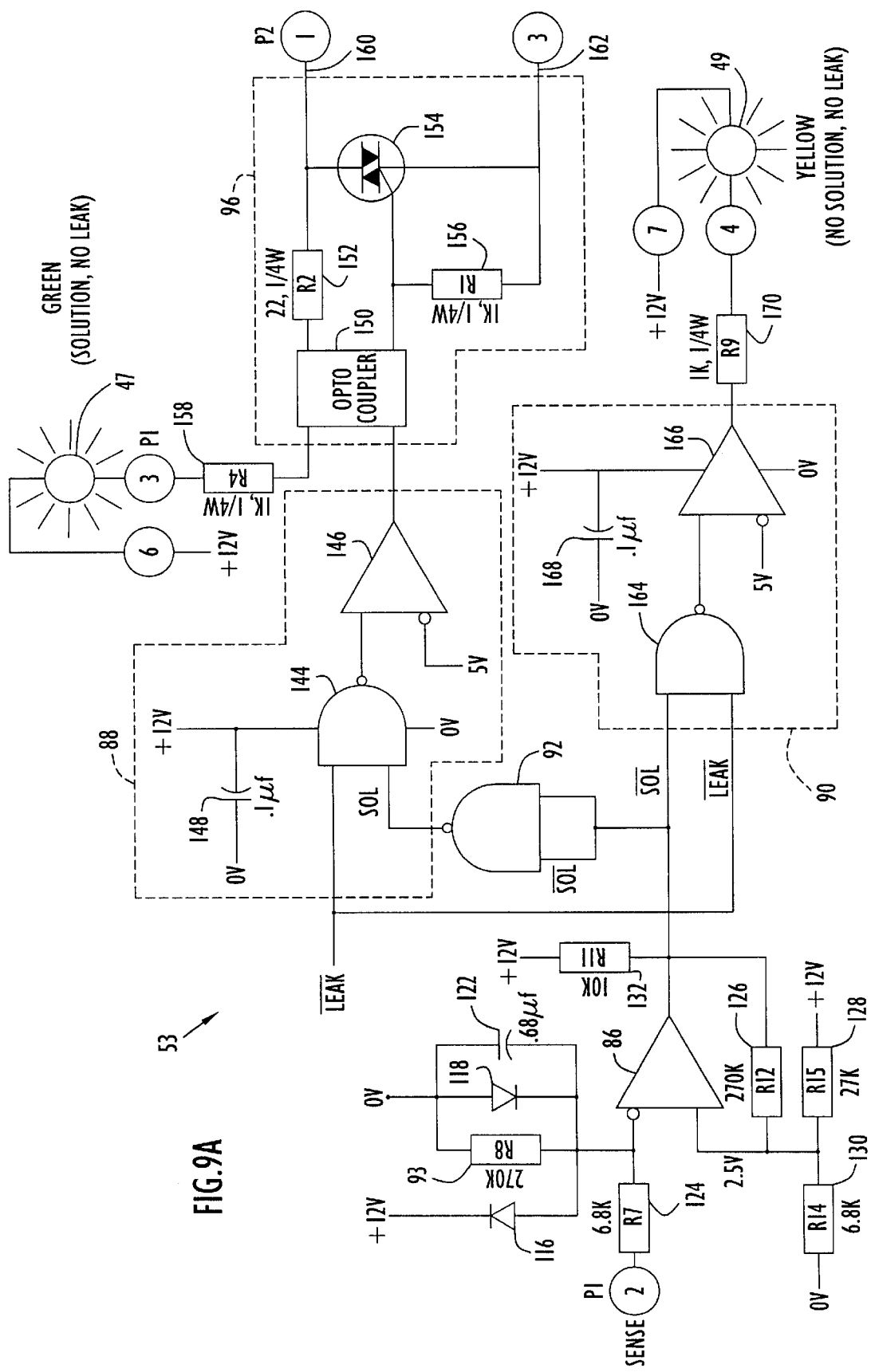
FIGS. 9A–9B are detailed electrical schematic diagrams of the condition circuit of FIG. 8.
Figure 9B:
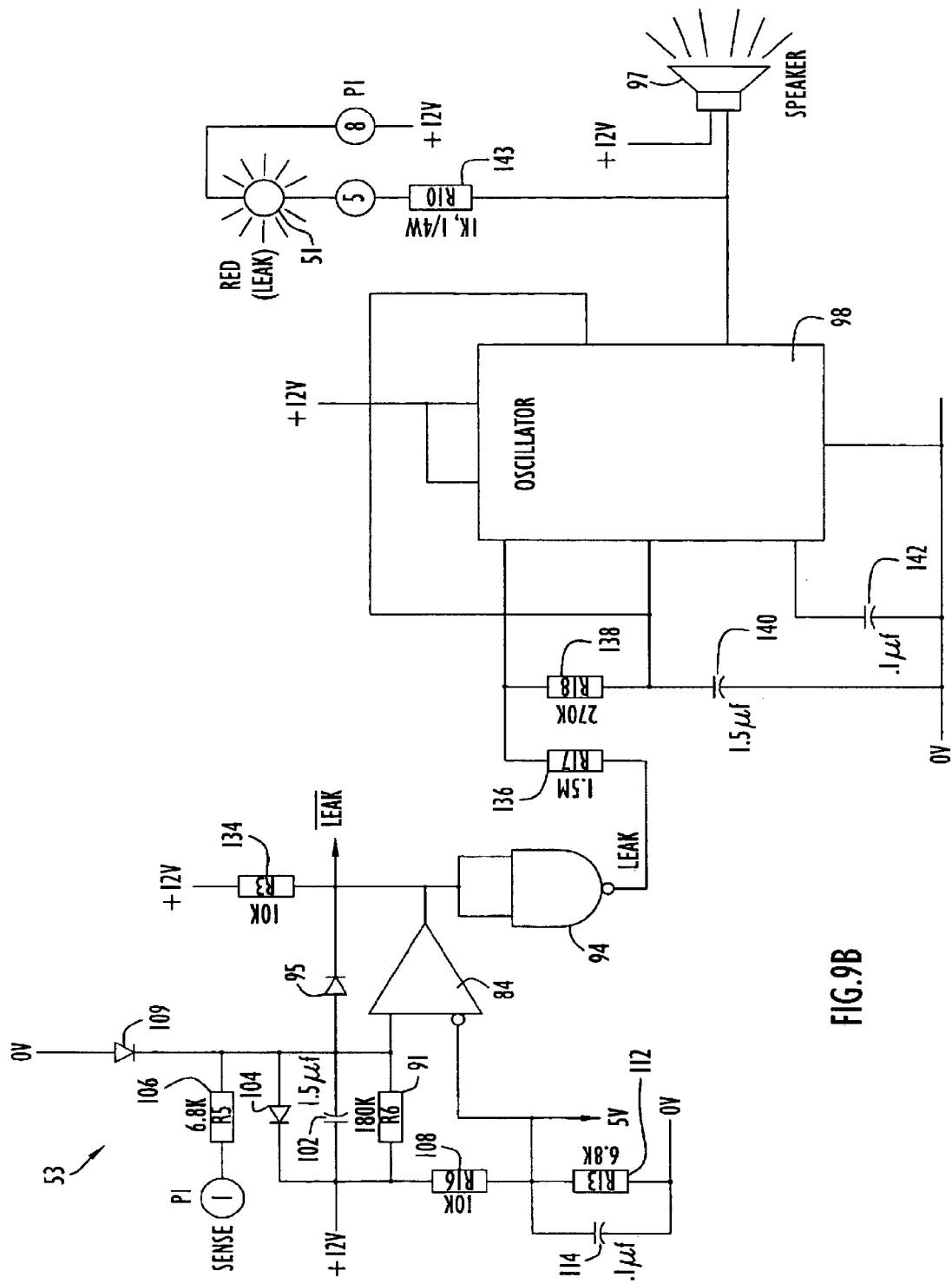

An exemplary condition circuit for detecting the presence of solution and leaks within the drape container is illustrated in FIGS. 8, 9A and 9B. Initially, the condition circuit prevents operation of the thermal treatment system in the event a drape is damaged (e.g., contains a leak) or not connected to the detection circuitry, or in the event solution is absent from the drape container. The condition circuit is coupled to the drape electrodes via pins 1 and 2 of circuit board 52. The presence of solution within the drape container causes current flow between the electrodes, while a leak facilitates current flow between the electrodes and ground as described above. Accordingly, the current flow causes a voltage change at pins 1 and 2 of the circuit board, thereby enabling detection of solution and leaks by the condition circuit. In particular, the condition circuit includes comparators 84,86, logic circuitry 88,90, inverters 92, 94, a power switch 96 and an oscillator 98. Pin 1 of circuit board 52 is connected to the non-inverting input of comparator 84, while that input is further connected to a resistor 91 (e.g., 180K Ohm) disposed in series with a supply voltage (e.g., 12V DC). The non-inverting input of comparator 84 is further coupled to additional circuitry (FIG. 9B) (e.g., a resistor 106 (e.g., 6.8K Ohm) connected in series with pin 1, a resistor 108 (e.g., 10K Ohm) coupled to resistor 91 and the supply voltage, a diode 104 connected in parallel with resistor 91, a capacitor 102 (e.g., 1.5 $\mu f$) connected in parallel with resistor 91 and diode 104, and a diode 109 connected between the non-inverting input and a ground potential) to protect the circuit from damage in the event an external voltage is applied to pins 1 and 2 and to provide filtering to prevent a response to noise. A diode 95 is disposed in a feedback path of comparator 84 to maintain the state of a particular condition as described below. The inverting input of comparator 84 is similarly coupled to additional circuitry (FIG. 9B) (e.g., a resistor 112 (e.g., 6.8K Ohm) connected between resistor 108 and a ground potential, and a capacitor 114 (e.g., 0.1 $\mu$f) connected in parallel with resistor 112) to enhance circuit performance. Resistors 108 and 112 basically provide the comparator inverting input with a reference voltage (e.g., 5V DC). Comparator 84 determines the presence of a drape container leak by comparing the input of pin 1 to the reference voltage (e.g., 5V DC). If pin 1 exceeds the reference voltage, the comparator provides a high level logic signal indicating the absence of a leak (e.g., the signal $\overline{\text{LEAK}}$ in the figures indicates the absence of a drape container leak when attaining a high logic level); otherwise a low level logic signal indicating the presence of a leak is produced by the comparator.

Pin 2 is connected to the inverting input of comparator 86, while that input is further connected to a resistor 93 (e.g., 270K Ohm) disposed between the comparator input and a ground potential. The inverting input is further coupled to additional circuitry (FIG. 9A) (e.g., a resistor 124 (e.g., 6.8K Ohm) connected in series with pin 2, a diode 116 connected in series with a supply voltage (e.g., 12V DC), a diode 118 connected in parallel with resistor 93, and a capacitor 122 (e.g., 0.68 $\mu$f) connected in parallel with resistor 93 and diode 118) to protect the circuit from damage in the event an external voltage is applied to pins 1 and 2 and to provide filtering to prevent a response to noise. The non-inverting input of comparator 86 is coupled to additional circuitry (FIG. 9A) (e.g., a resistor 126 (e.g., 270K Ohm) connected in a comparator feedback path, a resistor 128 (e.g, 27K Ohm) connected between the non-inverting input and a supply voltage (e.g., 12V DC), a resistor 130 (e.g., 6.8K Ohm) connected between the non-inverting input and a ground potential, and a resistor 132 (e.g., 10K Ohm) connected between a supply voltage (e.g., 12V DC) and the comparator output) that basically provides a reference voltage (e.g., 2.5V DC) for the comparator non-inverting input. Comparator 86 determines the presence of solution within the drape container by comparing the input of pin 2 with the reference voltage. If the reference voltage (e.g., 2.5V) exceeds pin 2, the comparator produces a high level logic signal indicating the absence of solution within the drape container (e.g., the signal $\overline{\text{SOL}}$ in the figures indicates the absence of solution within the drape container when attaining a high logic level); otherwise a low level logic signal indicating the presence of solution is produced.

The output of comparator 84 is coupled to inverter 94, to an input of logic circuitry 88 and to an input of logic circuitry 90. The comparator output is further coupled to additional circuitry (FIG. 9B) (e.g., a resistor 134 (e.g., 10K Ohm) connected between the comparator output and a supply voltage (e.g., 12V DC)) to enhance circuit performance. Inverter 94 is in the form of a NAND gate (FIG. 9B) and inverts the comparator output. Since comparator 84 provides a low level logic signal in response to the presence of a leak as described above, inverter 94 inverts the comparator output to provide a high level logic signal in response to a leak (e.g., the signal LEAK in the figures indicates the presence of a drape container leak when attaining a high logic level). The inverter is connected to a timer 98 that serves as a low frequency oscillator and is actuated by the high level logic signal produced by inverter 94 in response to the presence of a leak. Additional circuitry (FIG. 9B) (e.g., a resistor 136 (e.g., 1.5M Ohm) connected in series with the NAND gate output, a resistor 138 (e.g., 270K Ohm) connected between timer inputs, a capacitor 140 (e.g., 1.5 $\mu$f) connected between resistor 138 and a ground potential, and a capacitor 142 (e.g., 0.1 $\mu$f) connected between a timer input and the ground potential) is connected to and/or between the inverter and oscillator to enhance actuation of the oscillator in response to a high level logic signal from the inverter. The oscillator output is coupled to a reference terminal of a speaker 97 and to pin 5 for actuating red diode 51. A resistor 143 (e.g., 1K Ohm) is disposed between pin 5 and the oscillator output, while a speaker positive terminal is connected to a supply voltage (e.g., 12V DC). The oscillator output is in the form of a pulse train that provides periodic low level logic signals. The low level signals provide a sufficient voltage differential to enable the supply voltages of the red diode (e.g., 12V DC of pin 8) and speaker (e.g., 12V DC of the speaker positive terminal) to drive those devices. Thus, the oscillator produces a pulse train that enables the diode to flash and the speaker to beep at rates proportional to the pulse train frequency when a leak is present in the drape container.

Conversely, when a leak is absent from the drape container, comparator 84 provides a high level logic signal as described above. Inverter 94 inverts the comparator output to provide a low level logic signal in response to the absence of a leak. The low level logic signal is insufficient to actuate oscillator 98, thereby disabling red diode 51 and speaker 97 when a leak is not present within the drape container.

Logic circuitry 88 determines the presence of conditions to enable the heater (e.g., solution is present within the drape container without a leak). The logic circuitry is coupled to outputs of comparators 84 and 86. An inverter 92 in the form of a NAND gate (FIG. 9A) is disposed between logic circuitry 88 and comparator 86 to invert the comparator output. Since comparator 86 produces a low level logic signal in response to the presence of solution within the drape container, inverter 92 inverts the comparator output to provide a high level logic signal in response to the presence of solution (e.g., the signal SOL within the figures indicates the presence of solution within the drape container when attaining a high logic level). Logic circuitry 88 combines the signals (e.g., $\overline{\text{LEAK}}$, SOL) from comparator 84 and inverter 92, indicating leak and solution conditions, and provides a signal to illuminate green diode 47 and actuate power switch circuitry 96 to enable heater 70 in response to the signals indicating the presence of solution without a leak in the drape container.

Logic gate circuitry 88 (FIG. 9A) includes a NAND gate 144 and a comparator 146. The NAND gate receives output signals from comparator 84 and inverter 92 and produces a low level logic signal in response to the signals indicating the presence of solution in the drape container without a leak. The NAND gate output is connected to the non-inverting input of comparator 146, while the comparator inverting input is connected to a reference voltage (e.g., 5V DC). The comparator produces a low level logic signal in response to a low NAND gate output in order to drive power switch circuitry 96 to enable heater 70 when solution is present within the drape container without a leak. NAND gate 144 is further coupled to additional circuitry (e.g., a ground potential coupled to a gate terminal, a supply voltage (e.g., 12V DC) coupled to another gate terminal with a capacitor 148 (e.g., 0.1 µf) connected between that gate terminal and a ground potential) to enhance gate operation.

Power switch circuitry 96 includes an optocoupler 150 and a triac 154. The triac is connected between conductors 160, 162 of plug 76 and has a gate terminal coupled to an output of the optocoupler. An optocoupler input is coupled to circuit board pin 3 and, hence, to green diode 47 disposed between circuit board pins 3 and 6, while a resistor 158 (e.g., 1K Ohm) is connected between pin 3 and the optocoupler. The output of comparator 146 indicating drape container conditions is connected to another input of the optocoupler to drive the power switch circuitry in response to the presence of solution without a leak in the drape container as described above. A resistor 152 (e.g., 22 Ohms) is connected to an optocoupler output and in series with the triac, while a resistor 156 (e.g., 1 K Ohm) is connected between the triac gate terminal and conductor 162 of plug 76. A low level logic signal produced by comparator 146 provides a ground that enables the optocoupler input to receive appropriate current to produce outputs that drive the triac. Thus, the low level logic signal from comparator 146 enables actuation of the green diode and triac to indicate the presence of solution without a leak in the drape container and to enable the heater, respectively. The triac provides signals to heat control circuitry 110 (FIG. 7) via plug 76 to control actuation of the heater as described above.

Conversely, when a leak is present within, or solution is absent from, the drape container, comparators 84, 86 provide signals that enable NAND gate 144 to produce a high level logic signal. Comparator 146 generates a high level logic signal in response to the high level NAND gate output, thereby preventing actuation of power switch 96, green diode 47 and heater 70 when a leak is present within, or solution is absent from, the drape conatiner.

Logic circuitry 90 determines the presence of conditions to illuminate yellow diode 49 (e.g., neither solution nor a leak is present within the drape container). The logic circuitry is coupled to the outputs of comparators 84 and 86. Logic circuitry 90 combines the signals (e.g., $\overline{LEAK}$, $\overline{SOL}$) from comparators 84, 86 indicating drape container conditions and provides a signal to actuate yellow diode 49 in response to the comparator signals indicating the absence of solution and a leak within the drape container.

Logic circuitry 90 (FIG. 9A) includes a NAND gate 164 and a comparator 166. The NAND gate receives output signals from comparators 84 and 86 and produces a low level logic signal in response to the comparator signals indicating the absence of solution and a leak within the drape container. The NAND gate output is connected to the non-inverting input of comparator 166, while the comparator inverting input is connected to a reference voltage (e.g., 5V DC). The comparator provides a low level logic signal in response to a low NAND gate output in order to illuminate yellow diode 49. The yellow diode is disposed between circuit board pins 4 and 7 with a resistor 170 (e.g., 1K Ohm) connected between pin 4 and the comparator output. A low level logic signal produced by comparator 166 provides a sufficient voltage differential to enable pin 7 connected to a supply voltage (e.g., 12V DC) to illuminate yellow diode 49. Conversely, when a leak or solution is present within the drape container, comparators 84, 86 provide signals that enable NAND gate 164 to produce a high level logic signal. Comparator 166 generates a high level logic signal in response to the high level NAND gate output, thereby preventing illumination of yellow diode 49 when a leak or solution is present within the drape container.

The condition circuit basically controls system operation in response to detected drape container conditions. The circuit is arranged to enable signals from comparators 84, 86 to selectively facilitate a particular action (e.g., illuminate the red diode and speaker, enable the green diode and heater, or illuminate the yellow diode) in response to the occurrence of corresponding conditions for that action. In other words, a particular action is initiated by the condition circuit in response to the occurrence of corresponding conditions, while remaining actions are disabled. Thus, the green diode and heater are enabled by the condition circuit in response to the presence of solution without a leak in the drape container, and are disabled during occurrence of other drape container conditions (e.g., a leak or no solution within the drape container). Enablement and disablement of the yellow diode and red diode and speaker are facilitated in a similar manner with respect to their corresponding conditions. The condition circuit and/or circuit board may further include circuitry to record the time and/or date when the system or heater is enabled and disabled or any other information. The stored information may be retrieved for hospital records or to assist in evaluating system performance.

The manner in which the condition circuit operates is described, by way of example only, with reference to FIG. 8. Initially, when solution is absent from the drape container, no current flow exists between electrodes 22, 24 (FIG. 2) and the voltage applied to pins 1 and 2 of circuit board 52 is maintained at twelve and zero volts, respectively. These conditions are similarly present when the drape is disconnected from or incompatible with the system. The output of comparators 84 and 86 are high (e.g., indicating no leak and no solution), thereby enabling logic circuitry 90 to illuminate yellow diode 49 as described above, while the heater, speaker and green and red diodes are disabled as described above.

In the event that solution is present without a leak in the drape container, a conductive path is formed between the electrodes and, hence, between pins 1 and 2 of the circuit board. Since the conductive path has a low resistance relative to resistors 91 and 93, these resistors basically form a voltage divider with resistor 91 connected to the supply voltage of 12V DC and resistor 93 connected to ground. The voltage divider provides each pin 1 and 2 with approximately 7.2 V DC. Accordingly, the output of comparator 84 is high (e.g., indicating no leak), while the output of comparator 86 is low (e.g., indicating the presence of solution), thereby enabling logic circuitry 88 to illuminate the green diode and actuate the power switch to enable the heater, while the speaker and red and yellow diodes are disabled as described above.

A leak within the drape container forms a conductive path between the electrodes (e.g., and, hence, pins 1 and 2) and ground. Thus, the potential of pin 1 is reduced below the comparator reference potential (e.g., 5V DC), thereby causing comparator 84 to produce a low level logic signal. Diode 95 provides feedback to maintain the state of the leak condition until power is disabled. The low output of comparator 84 is inverted by inverter 94, thereby actuating oscillator 98. The oscillator illuminates red diode 51 and actuates speaker 97 to provide an audio leak indication, while the heater and green and yellow diodes are disabled as described above. The output of comparator 86 has no bearing on leak detection and is ignored with respect to actuation of the oscillator. The condition circuit basically generates signals to control the heater and provides visual and audio indications to inform a user of the drape container status.

The condition circuitry may employ any conventional or other components that perform the above-described functions. The reference voltages utilized by comparators 84, 86 to detect drape container conditions may be any suitable voltages. By way of example only, the reference voltages utilized by those comparators in the condition circuit are derived from properties of saline or salt-water type solutions. Further, the reference voltages may be adjusted to account for objects placed in the basin. For example, placement of conductive objects (e.g., instruments, stainless steel pitchers, etc.) within the basin may establish a path for current flow between the electrodes irrespective of the presence of solution, thereby enabling the condition circuit to indicate erroneous conditions. Accordingly, the reference voltages may be adjusted to differentiate between current flow initiated by solution and the current flow initiated by a conductive object. Alternatively, conductive objects may be utilized in combination with and placed on a stand disposed within the basin to elevate the objects above the electrodes and basin floor in a manner similar to that disclosed in U.S. Pat. No. 6,087,636.

Operation of the thermal treatment system is described with reference to FIGS. 1, 4, 7 and 8. Initially, drape 17 is placed over the top surface of the thermal treatment system and disposed in basin 33 to form a drape receptacle. Connector 40 of the drape is inserted within receptacle 46 of wiring housing 44 to connect the drape to detection circuitry 120 to facilitate detection of drape container conditions. Power switch 37 is actuated and detection circuitry 120 senses no voltage change across the electrodes (e.g., and, hence, pins 1 and 2 of the circuit board), thereby indicating the absence of solution and a leak within the drape container as described above. The detection circuitry illuminates yellow diode 49, while disabling the heater, speaker and red and green diodes as described above. A sterile medium is disposed within the drape receptacle and a desired temperature for the medium is entered into the system by the user via controller 38. The sterile medium forms a conductive path between the electrodes that affects the voltage thereof (e.g., and, hence, of pins 1 and 2 of the circuit board). Detection circuitry 120 senses the voltage change indicating the presence of solution without a leak in the drape container, and illuminates green diode 47 and enables actuation of the heater, while disabling the speaker and red and yellow diodes as described above. Temperature controller 38 subsequently controls power to heater 70 in accordance with a comparison of the desired temperature with a temperature measured by temperature sensor 72 as described above.

When a leak occurs within the drape container, a conductive path is formed between the electrodes and the basin serving as ground, thereby affecting the voltage of the electrodes (e.g., and, hence, of pins 1 and 2 of the circuit board). The detection circuitry senses the voltage change indicating a leak within the drape container, and provides an audio indication via speaker 97, flashes red diode 51 and disables the heater and yellow and green diodes as described above.

Figure 10:
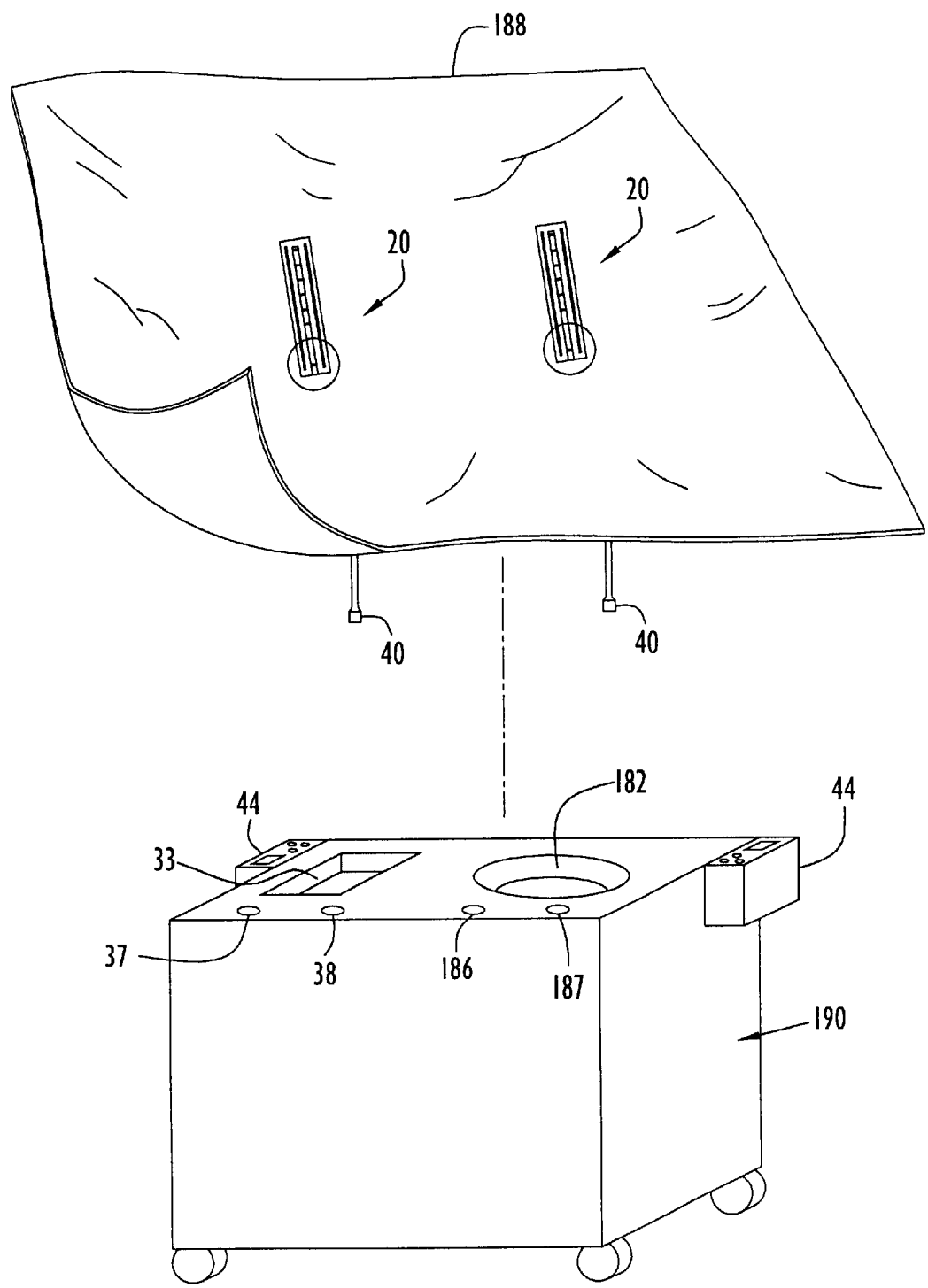
FIG. 10 is an exploded view of a surgical drape including plural sensing devices and disposed over a plural basin thermal treatment system according to the present invention.

It is to be understood that the present invention may be employed for thermal treatment systems including a plurality of basins that either heat or cool the sterile medium. An exemplary plural basin system and corresponding drape according to the present invention are illustrated in FIG. 10. Specifically, the plural basin system includes an integral assembly 190 including warming basin 33 and a substantially circular cooling basin 182 to thermally treat sterile liquid. The system includes power switches 37, 186 and controllers 38, 187 to control operation of the warming and cooling basins, respectively. The assembly further houses the heating and refrigeration devices and control circuitry (not shown) for the individual basins to thermally treat those basins and liquid contained therein as described above. A drape 188, substantially similar to drape 17 described above, is placed over the system and within each basin to form a drape receptacle therein as described above. Sensing devices 20 are affixed at appropriate locations on the drape in the manner described above for insertion within a corresponding basin to detect drape container conditions within that basin. Electrode signals are conveyed from each sensing device disposed within a basin to a corresponding individual condition circuit associated with that basin to determine drape container conditions and provide signals to control the basin in substantially the same manner described above. The assembly may further include a wiring housing 44 associated with each basin to receive connector 40 of the associated sensing device and transfer signals between that housing and a corresponding individual condition circuit in substantially the same manner described above. Each wiring housing typically includes diodes 47, 49, 51 to indicate drape container conditions within a corresponding basin and a receptacle 46 to receive a corresponding connector 40 as described above. The individual basins each basically function in substantially the same manner as the single basin system described above, where the plural basins may be individually controlled or collectively controlled (e.g., all basins enabled or disabled) in response to drape container conditions.

Figure 11:
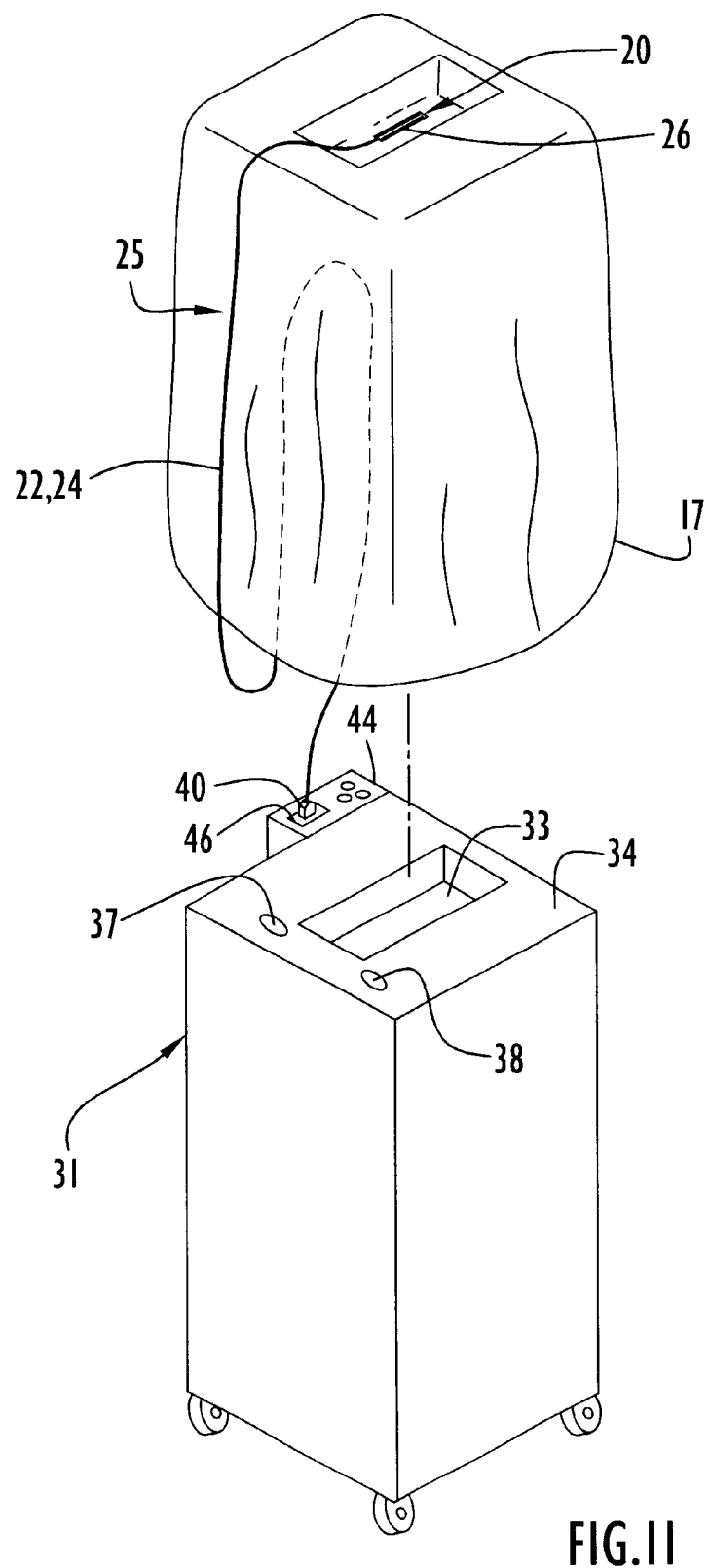
FIG. 11 is an exploded view in perspective of an alternative surgical drape including a sensing device and disposed over a thermal treatment system according to the present invention.

In addition, the sensing device electrodes may alternatively traverse a drape edge to extend between the sterile and non-sterile drape surfaces and interface detection circuitry disposed within the cabinet as illustrated in FIG. 11. Initially, the thermal treatment system and drape are substantially similar to the system and drape described above for FIG. 1, except that sensing device 20 traverses a drape bottom edge (e.g., without being disposed through the drape) to extend between sterile and non-sterile drape surfaces. Specifically, the thermal treatment system includes cabinet 31, wiring housing 44, power switch 37, controller 38 and warming basin 33 recessed into cabinet top surface 34, each as described above. Drape 17 is typically positioned over the thermal treatment system with a portion of the drape disposed in basin 33 to form a drape receptacle as described above. The drape forms a sterile field above the basin to maintain sterility of the sterile medium. Drape 17 includes sensing device 20 to detect the presence of liquid and leaks within the drape container. Sensing device 20 is in the form of a pair of electrodes 22, 24 that are affixed to strip 25 with the strip proximal portion secured to an intermediate section of the drape sterile surface (e.g., the strip proximal portion may be disposed within pouch 26). The distal ends of the electrodes are attached to plug 40 that interfaces detection circuitry within the thermal treatment system as described above. Strip 25 extends from the drape container along the drape sterile surface covering the basin and cabinet walls to a drape bottom or peripheral edge. The strip traverses the drape bottom edge to pass from the sterile to the non-sterile drape surface, and further extends beneath the drape to wiring housing 44 attached to cabinet 31. The wiring housing includes receptacle 46 for receiving connector 40, thereby connecting the drape to detection circuitry disposed within the thermal treatment system as described above. The electrodes provide signals to the detection circuitry to facilitate detection of liquid and/or leaks within the drape container as described above. Further, the sensing devices of plural basin drape 188 may be fastened to that drape with respective electrode strips traversing a drape edge (e.g., without being disposed through the drape) to extend between the sterile and non-sterile drape surfaces for connection to corresponding detection circuitry disposed within the plural basin system in substantially the same manner described above.

It will be appreciated that the embodiments described above and illustrated in the drawings represent only a few of the many ways of implementing a medical solution thermal treatment system and method of controlling system operation in accordance with detection of solution and leaks in surgical drape containers.

The warming, cooling and plural basin systems and their corresponding cabinets, assemblies or housings may be of any shape or size and may be constructed of any suitable materials. The plural basin system may include any quantity of heating and/or cooling basins in any combinations. The basins of the systems may be of any shape or size, may be constructed of any suitable thermal conducting materials (e.g., stainless steel) and may be disposed at any suitable locations on or within the housings. The systems may include any conventional or other heating and/or refrigeration units to thermally treat the sterile medium or other substance to any desired temperature. The heating unit may include any conventional or other heating device and components to control heating of a basin to any desired temperature (e.g., preferably to temperatures near (e.g., above, at or below) body temperature, such as temperatures in the approximate range of 60° F.–160° F.). The heater may be of any quantity (e.g., at least one), shape or size, and may include any configuration (e.g., strips, bars, segments, etc.) that covers the entirety or any portion of a basin. The heater may be attached to a basin via any conventional or other fastening techniques (e.g., any type of adhesives, brackets, etc.). In addition, the heater may be implemented by any conventional or other type of heater or heating element (e.g., heating coils, etc.) that may be disposed on or proximate a basin at any suitable locations.

The cooling unit may include any conventional or other cooling or refrigeration device and components to control cooling of a basin to any desired temperature (e.g., preferably to temperatures near or below the freezing temperature of the sterile liquid or medium, such as temperatures in the approximate range of –32° F. to 32° F.). The various power switches and controllers of the systems may be implemented by any conventional or other power and control devices and may be disposed on the systems at any suitable locations.

The temperature sensor maybe implemented by any conventional or other temperature sensing device (e.g., infrared, RTD, etc.) and may be disposed at any location on or proximate a basin or within the systems. The basins of the systems may be disposed in any arrangement or at any suitable locations on the systems. The systems may thermally treat (e.g., heat or cool) any type of medium or liquid, while a cooling basin may further include any type of conventional or other dislodgement mechanism, such as those described in the aforementioned patents.

The wiring housing may be of any quantity, shape or size, may be constructed of any suitable materials, and may be disposed at any suitable locations on the systems. The wiring housing and/or systems may include any suitable conductors or other medium (e.g., wireless, fiberoptics, etc.) to transfer signals between system components. The wiring housing may include any type of receptacle disposed at any suitable location on the wiring housing or systems to interface the drape sensing device. The wiring housing may include any quantity of any type of indicator (e.g., audio, speech synthesis, LED, display screen with text or images, etc.) to indicate the drape container status. The indicator may be disposed on the wiring housing or systems at any suitable locations. The diodes may be of any quantity or color, may be disposed at any suitable locations on the wiring housing or systems and may be illuminated in any desired fashion or pattern (e.g., flashing, continuous illumination, etc.). A drape container or other condition may be associated with any quantity of any diodes of any color (e.g., the same or different colors in any desired combinations).

The drapes employed with the heating, cooling and plural basin systems maybe of any size or shape, and may be constructed of any suitable materials. The drapes are preferably transparent or translucent to facilitate manipulation of controls through the drape, however, these drapes may have any degree of transparency (e.g., including opaque). The drapes may be manipulated in any fashion with any portions of the drapes serving as a drape receptacle within a corresponding basin. The drapes may be of sufficient size to accommodate and form drape receptacles within any quantity of thermal treatment system basins.

The sensing device may include any quantity of electrodes or electrode strips disposed at any suitable locations on a drape. The electrodes may be constructed of any suitable conductive materials. The electrode strip maybe of any shape or size, and may be constructed of any suitable materials. The electrodes may be fastened to the strip at any suitable locations via any conventional or other fastening techniques. The pouch may be of any quantity, shape or size, may be constructed of any suitable materials, may contain any portions of the electrodes or electrode strip and may be fastened to the drape at any suitable locations via any conventional or other fastening techniques. The flap may be of any quantity, shape or size, may be attached to the drape at any suitable locations via any conventional or other fastening techniques to form the pouch and may be constructed of any suitable materials. The seams may be disposed on the flap at any suitable locations to attach the flap to the drape to form the pouch. The flap may include any quantity of openings or slots of any shape or size disposed in any suitable locations on the flap or pouch and arranged in any fashion to enable liquid within the drape container to contact the electrodes. Alternatively, the sensing device or electrode strip maybe attached to the drape (i.e., without the pouch) via the patch or any other securing mechanisms (e.g., adhesives, welding, etc.) to sense drape container conditions.

The drape opening may be of any quantity, shape or size and may be defined in the drape at any suitable locations. The patch may be of any quantity, shape or size, may be constructed of any suitable materials and may be disposed at any suitable locations on the drape. The drape may include any quantity of openings and corresponding patches disposed on or attached to either or both of the sterile and non-sterile drape surfaces. The drape may include any quantity of sensing devices for a corresponding basin where the sensing device signals may be combined in any fashion (e.g., at least one device detecting liquid, combined logically (e.g., AND, OR, etc.), etc.) to determine occurrence of drape container conditions (e.g., solution or leaks present). The sensing device plug may be implemented by any conventional or other plug or connector where the electrode traces may be disposed at any locations on the plug. Alternatively, the electrode strip or other objects may traverse a drape peripheral or other edge (e.g., without being disposed through the drape) to extend between the sterile and non-sterile drape surfaces.

The electrical connections may include any quantity of components (e.g., power cord, fuses, conductors, connectors, power supply, circuit board, diodes, etc.) arranged in any desired fashion, where each component may be implemented by any conventional or other component performing the described function. The control circuit may be disposed within the systems at any suitable locations and may be implemented by any conventional or other circuitry components arranged in any desired fashion to perform the described functions. The plugs connecting thermal control circuitry to the detection circuitry may be implemented by any conventional or other connectors for transferring signals. The temperature controller may be implemented by any conventional or other temperature controller and include any desired devices for entering a temperature (e.g., buttons, keypad, etc.). The basin power switches of the systems may be implemented by any conventional or other switching device, while the fuses may be implemented by any conventional fuse or other limiting device and may be configured for any current or voltage levels. The wiring harness connector may be implemented by any conventional or other connector to facilitate component connections, while the power cord may be implemented by any conventional or other cord or cable and be configured to accommodate any desired power signals. The thermostat maybe implemented by any conventional switching type or limiting devices, such as a high limit thermostat, and may be disposed at any suitable location within the systems.

The circuit board housing the condition circuit may include any quantity of terminals or pins each associated with any desired signals or portion of the condition circuit. The circuit board may include any quantity of indicators disposed at any suitable locations to indicate the occurrence or status of any desired circuit portion or condition. The circuit board receptacle may be implemented by any conventional or other receptacle and be suitable for receiving any type of plug or connector to interface thermal control circuitry. The power supply may be implemented by any conventional or other power supply or source and provide any desired power signals, and may include any type of conventional or other receptacle for receiving any type of plug or connector to interface thermal control circuitry. The diodes or other indicators may be connected to the circuit board pins in any desired fashion. The circuit board may house the condition circuit and/or any other desired system circuitry. Further, the circuit board may include devices to record any types of information relating to system operation for subsequent retrieval and analysis (e.g., date and time of thermal treatment disablement and enablement, etc.).

The condition circuit may include any quantity of conventional or other components arranged in any desired fashion to perform the functions described herein. The circuit comparators may be implemented by any conventional or other comparators or comparing devices and may utilize any suitable reference potentials to detect solution, leaks or any other conditions. The inverters may be implemented by any conventional or other inverting devices (e.g., logic gates, circuitry, etc.) to invert circuit signals. The logic circuitry and corresponding logic gates maybe implemented by any logic gates or combinational logic (e.g., AND, OR, NAND, NOR, XOR, etc.) and/or circuitry (e.g., comparator, inverter, transistors, etc.) arranged in any desired fashion to combine signals to determine the occurrence of any conditions. The logic circuitry comparators maybe implemented by any conventional or other comparators or comparing devices and utilize any desired reference potentials. The oscillator may be implemented by any conventional or other timer or oscillating device producing outputs at any desired frequency. The oscillator may drive any type of device (e.g., speaker, speech synthesis, diode, etc.) to indicate the presence of a condition, while the indicator devices may alternatively be driven by any type of circuitry or mechanism. The speaker may be implemented by any conventional or other speaker or audio device and may provide any suitable audio indication (e.g., beep at any suitable periodic interval, continuous audio output, etc.).

The triac may be implemented by any conventional or other triac or relay type device to provide signals to thermal control circuitry for controlling thermal treatment of a basin. The condition circuit may include any additional circuitry (e.g., resistors, capacitors, inductors, diodes, supply and ground potentials, etc.) arranged in any fashion and including any desired electrical characteristic values (e.g., resistance, potential, capacitance, etc.) to facilitate circuit operation. The condition circuit signals may include any desired logic or voltage levels. The optocoupler may be implemented by any conventional or other optocoupler or other circuitry to control the triac to provide signals to the thermal control circuitry.

The plural basin system may include individual thermal control and detection circuitry associated with each basin to monitor drape container conditions and control basin operation. Alternatively, the plural basin system may include common thermal control and detection circuitry to control each basin in response to drape container conditions. The common circuitry may receive signals from each sensing device and control the basins individually or collectively in response to the drape container conditions. The common circuitry may process and combine the signals in any fashion (e.g., AND, OR, etc.) to determine conditions for controlling the basins. The detection circuitry of the systems may alternatively include a microprocessor to process electrode signals and control the diodes, heater, speaker or any other devices. In this case, electrode signals are converted to digital signals and compared by the microprocessor to threshold levels for each condition. The microprocessor may generate the appropriate control signals to control basin thermal devices and various indicators in accordance with the determined conditions.

The drape may facilitate placement of any types of objects (e.g., conductors, tubes or other fluid passages, various communication medium, etc.) through or around the drape in any manner (e.g., traverse any drape opening or drape edge, etc.) to enable communication or passage between the sterile and non-sterile sides of the drape without compromising the sterile field. Further, the electrodes or other communication medium may be connected to various sensors or any other types of measuring, analytical and/or control devices to measure, determine and/or indicate any types of conditions and/or control system operation in any desired fashion in response thereto.

It is to be understood that the terms "top", "bottom", "front", "rear", "side", "height", "length", "width", "upper", "lower" and the like are used herein merely to describe points of reference and do not limit the present invention to any particular orientation or configuration.

From the foregoing description, it will be appreciated that the invention makes available a novel medical solution thermal treatment system and method of controlling system operation in accordance with detection of solution and leaks in surgical drape containers wherein a surgical drape includes a sensing device to provide signals indicating drape container conditions to a thermal treatment system to facilitate control of system operation.

Having described preferred embodiments of a new and improved medical solution thermal treatment system and method of controlling system operation in accordance with detection of solution and leaks in surgical drape containers, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for detecting conditions within containers formed by surgical drapes during surgical procedures and controlling thermal treatment of said containers in response to said detected conditions, said system comprising:
   a thermal treatment unit to thermally treat a liquid and including a basin;
   a surgical drape, covering and substantially conforming to said basin, to serve as a drape container for said liquid;
   a sensing device including a plurality of conductors each disposed on a sterile drape surface within said drape container and extending therefrom to a non-sterile drape surface, wherein potentials of said conductors are responsive to contact between said conductors and said liquid and indicate conditions of said drape container, and wherein each of said drape container conditions corresponds to a different conductor potential and said drape container conditions include presence of a leak within said drape container;
   a controller to operate said thermal treatment unit to control a temperature of said basin; and
   a detection unit in communication with said sensing device to determine occurrence of said drape container conditions from said potentials of said conductors and to control said controller to operate said thermal treatment unit in accordance with said determined drape container conditions.

2. The system of claim 1 wherein said plurality of conductors includes a plurality of electrodes.

3. The system of claim 1 wherein said drape includes an opening defined therein to permit passage of said plurality of conductors therethrough and a material segment attached to a drape surface coincident said opening to seal said opening and secure said plurality of conductors within said drape container.

4. The system of claim 1 wherein said drape includes a receptacle attached to said sterile drape surface to contain a proximal portion of each said conductor, wherein said receptacle includes a series of openings defined therein to enable said liquid within said drape container to contact said plurality of conductors contained within said receptacle.

5. The system of claim 1 wherein said sensing device includes a connector to receive a distal end of each said conductor and couple said sensing device to said detection unit.

6. The system of claim 5 further including a wiring unit to facilitate connections between said sensing device and said detection unit, wherein said wiring unit includes a connector receptacle to receive said connector and couple said sensing device to said detection unit.

7. The system of claim 1 further including a plurality of indicators to indicate drape container conditions, wherein said indicators are actuable in response to control signals generated by said detection unit in accordance with said determined occurrence of said drape container conditions.

8. The system of claim 7 wherein at least one indicator includes a visual indicator to visually indicate occurrence of a drape container condition.

9. The system of claim 7 wherein at least one indicator includes an audio indicator to produce audio signals to indicate occurrence of a drape container condition.

10. The system of claim 1 wherein said detection unit disables said thermal treatment unit in response to said potentials of said conductors indicating presence of a leak or absence of said liquid within said drape container.

11. The system of claim 1 wherein said detection unit enables said thermal treatment unit in response to said potentials of said conductors indicating presence of said liquid and absence of a leak within said drape container.

12. The system of claim 1 wherein said thermal treatment unit is operative to cool said liquid in said drape container.

13. The system of claim 1 wherein said thermal treatment unit produces a heated liquid in said drape container.

14. The system of claim 1 further including:
   a plurality of said thermal treatment units to thermally treat said liquid and each including a basin, wherein said surgical drape covers and substantially conforms to each said basin to serve as said drape container for said liquid in each said basin;
   a plurality of said sensing devices each including a plurality of said conductors disposed on said sterile drape surface within a corresponding drape container and extending therefrom to a non-sterile drape surface;
   at least one controller to operate said thermal treatment units to control temperature of each said basin; and
   at least one detection unit in communication with each said sensing device to determine occurrence of drape container conditions within said each basin from said potentials of said conductors associated with that basin to control said at least one controller to operate said thermal treatment units in accordance with said determined drape container conditions.

15. A device for detecting conditions within a basin of a thermal treatment system during surgical procedures and facilitating control of thermal treatment of said basin and liquid contained therein in response to said detected conditions, said device comprising:
   a surgical drape to cover and substantially conform to said basin to serve as a drape container for said liquid; and
   a sensing device including a plurality of conductors each disposed on a sterile drape surface within said drape container and extending therefrom to a non-sterile drape surface, wherein potentials of said conductors are responsive to contact between said conductors and said liquid and indicate conditions of said drape container, and wherein each of said drape container conditions corresponds to a different conductor potential and said drape container conditions include presence of a leak within said drape container.

16. The detecting device of claim 15 wherein said plurality of conductors includes a plurality of electrodes.

17. The detecting device of claim 15 wherein said drape includes an opening defined therein to permit passage of said plurality of conductors therethrough and a material segment attached to a drape surface coincident said opening to seal said opening and secure said plurality of conductors within said drape container.

18. The detecting device of claim 15 wherein said drape includes a receptacle attached to said sterile drape surface to contain a proximal portion of each said conductor, wherein said receptacle includes a series of openings defined therein to enable said liquid within said drape container to contact said plurality of conductors contained within said receptacle.

19. The detecting device of claim 15 wherein said sensing device includes a connector to receive a distal end of each said conductor and couple said sensing device to said thermal treatment system.

20. The detecting device of claim 15 wherein:
said thermal treatment system includes a plurality of said basins to thermally treat said liquid; and
said drape covers and substantially conforms to each said basin to serve as said drape container for said liquid in each said basin, wherein said drape further includes a plurality of said sensing devices each including a plurality of said conductors disposed on said sterile drape surface within a corresponding drape container and extending therefrom to said non-sterile drape surface, and wherein potentials of said conductors associated with a drape container are responsive to contact between those conductors and said liquid and indicate conditions of that drape container.

21. In a thermal treatment system including a basin for thermally treating a liquid, a method of detecting conditions during surgical procedures within a container formed within said basin by a surgical drape and controlling thermal treatment of said container in response to said detected conditions, wherein said drape includes a sensing device with a plurality of conductors disposed on a sterile drape surface within said drape container and extending therefrom to a non-sterile drape surface, said method comprising the steps of:
(a) placing said surgical drape over said thermal treatment system to cover and substantially conform to said basin to serve as a drape container for said liquid;
(b) altering potentials of said conductors in response to contact between said conductors and said liquid to indicate conditions of said drape container, wherein each of said drape container conditions corresponds to a different conductor potential and said drape container conditions include presence of a leak within said drape container; and
(c) determining occurrence of said drape container conditions from said potentials of said conductors and controlling said thermal treatment system to thermally treat said basin in accordance with said determined drape container conditions.

22. The method of claim 21 wherein said plurality of conductors includes a plurality of electrodes, and step (b) further includes:
(b.1) altering potentials of said electrodes in response to contact between said electrodes and said liquid to indicate conditions of said drape container.

23. The method of claim 21 wherein said sensing device includes a connector to receive a distal end of each said conductor, and step (a) further includes:
(a.1) coupling said sensing device to said thermal treatment system via said connector.

24. The method of claim 23 wherein said thermal treatment system further includes a wiring unit to facilitate connections between said sensing device and said thermal treatment system, wherein said wiring unit includes a connector receptacle to receive said connector, and step (a.1) further includes:
(a.1.1) coupling said sensing device to said thermal treatment system by inserting said connector within said connector receptacle.

25. The method of claim 21 wherein said thermal treatment system further includes a plurality of indicators to indicate drape container conditions, and step (c) further includes:
(c.1) generating control signals to selectively actuate said plurality of indicators in accordance with said determined occurrence of said drape container conditions.

26. The method of claim 25 wherein at least one indicator includes a visual indicator, and step (c.1) further includes:
(c.1.1) visually indicating occurrence of a drape container condition via said visual indicator.

27. The method of claim 25 wherein at least one indicator includes an audio indicator, and step (c.1) further includes:
(c.1.1) producing audio signals to indicate occurrence of a drape container condition via said audio indicator.

28. The method of claim 21 wherein step (c) further includes:
(c.1) disabling thermal treatment of said basin in response to said potentials of said conductors indicating presence of a leak or absence of said liquid within said drape container.

29. The method of claim 21 wherein step (c) further includes:
(c.1) enabling thermal treatment of said basin in response to said potentials of said conductors indicating presence of said liquid and absence of a leak within said drape container.

30. The method of claim 21 wherein said thermal treatment system includes a plurality of said basins, and step (a) further includes:
(a.1) placing said surgical drape over said thermal treatment system to cover and substantially conform to each said basin to serve as a drape container for said liquid, wherein said surgical drape includes a plurality of said sensing devices each including a plurality of said conductors disposed on said sterile drape surface within a corresponding drape container and extending therefrom to said non-sterile drape surface;
step (b) further includes:
(b.1) altering potentials of said conductors of a corresponding drape container in response to contact between those conductors and said liquid to indicate conditions of that drape container; and
step (c) further includes:
(c.1) determining occurrence of conditions of each said drape container from said potentials of said conductors associated with that drape container and controlling said thermal treatment system to thermally treat said basins in accordance with said determined drape container conditions.

31. A method of detecting conditions within a basin of a thermal treatment system during surgical procedures and facilitating control of thermal treatment of said basin and liquid contained therein in response to said detected conditions, said method comprising the steps of:
(a) forming a surgical drape to cover and substantially conform to said basin to serve as a drape container for said liquid; and
(b) disposing a sensing device including a plurality of conductors on a drape portion serving as said drape container with said conductors disposed on a sterile drape surface within said drape container and extending therefrom to a non-sterile drape surface, wherein potentials of said conductors are responsive to contact between said conductors and said liquid and indicate conditions of said drape container, and wherein each of said drape container conditions corresponds to a different conductor potential and said drape container conditions include presence of a leak within said drape container.

32. The method of claim 31 wherein said plurality of conductors includes a plurality of electrodes, and step (b) further includes:

(b.1) disposing said electrodes on said sterile drape surface within said drape container, wherein said electrodes extend between sterile and non-sterile drape surfaces.

33. The method of claim 31 wherein step (b) further includes:
(b.1) defining an opening within said drape to permit passage of said plurality of conductors therethrough; and
(b.2) attaching a material segment to a drape surface coincident said opening to seal said opening and secure said plurality of conductors within said drape container.

34. The method of claim 31 wherein step (a) further includes:
(a.1) attaching a receptacle to said sterile drape surface to contain a proximal portion of each said conductor, wherein said receptacle includes a series of openings defined therein to enable said liquid within said drape container to contact said plurality of conductors contained within said receptacle.

35. The method of claim 31 wherein step (b) further includes:
(b.1) placing a distal end of each said conductor within a connector to facilitate coupling of said sensing device to said thermal treatment system.

36. The method of claim 31 wherein said thermal treatment system includes a plurality of said basins to thermally treat said liquid, and step (a) further includes:
(a.1) forming said drape to cover and substantially conform to each said basin to serve as said drape container for said liquid in each said basin; and
step (b) further includes:
(b.1) disposing a sensing device including a plurality of conductors on each drape portion serving as a drape container with said conductors of each sensing device disposed on said sterile drape surface within a corresponding drape container and extending therefrom to said non-sterile drape surface, wherein potentials of said conductors associated with a drape container are responsive to contact between those conductors and said liquid and indicate conditions of that drape container.

37. A system for detecting conditions within containers formed by surgical drapes during surgical procedures and controlling thermal treatment of said containers in response to said detected conditions, said system comprising:
thermal treatment means for thermally treating a liquid and including a basin;
a surgical drape, covering and substantially conforming to said basin, to serve as a drape container for said liquid;
sensing means for sensing conditions within said drape container, wherein said sensing means includes a plurality of conducting means for maintaining a potential, wherein said plurality of conducting means are disposed on a sterile drape surface and within said drape container and extend therefrom to a non-sterile drape surface, and wherein said potentials of said plurality of conducting means are responsive to contact between said plurality of conducting means and said liquid and indicate conditions of said drape container, and wherein each of said drape container conditions corresponds to a different conducting means potential and said drape container conditions include presence of a leak within said drape container;
control means for operating said thermal treatment means to control a temperature of said basin; and
detection means in communication with said sensing means for determining occurrence of said drape container conditions from said potentials of said plurality of conducting means and for controlling said control means to operate said thermal treatment means in accordance with said determined drape container conditions.

38. The system of claim 37 further including condition indicating means for indicating drape container conditions, wherein said condition indicating means is actuable in response to control signals generated by said detection means in accordance with said determined occurrence of said drape container conditions.

39. The system of claim 37 wherein said detection means includes thermal control means for disabling said thermal treatment means in response to said potentials of said plurality of conducting means indicating presence of a leak or absence of said liquid within said drape container.

40. The system of claim 37 wherein said detection means includes thermal control means for enabling said thermal treatment means in response to said potentials of said plurality of conducting means indicating presence of said liquid and absence of a leak within said drape container.

41. The system of claim 37 further including:
a plurality of said thermal treatment means for thermally treating said liquid and each including a basin, wherein said surgical drape covers and substantially conforms to each said basin to serve as said drape container for said liquid in each said basin;
a plurality of said sensing means each including a plurality of said conducting means disposed on said sterile drape surface of a corresponding drape container and extending therefrom to said non-sterile drape surface;
at least one control means for operating said plurality of thermal treatment means to control temperature of each said basin; and
at least one detection means in communication with each said sensing means for determining occurrence of drape container conditions within said each basin from said potentials of said plurality of conducting means associated with that basin to control said at least one control means to operate said plurality of thermal treatment means in accordance with said determined drape container conditions.

42. A device for detecting conditions within a basin of a thermal treatment system during surgical procedures and facilitating control of thermal treatment of said basin and liquid contained therein in response to said detected conditions, said device comprising:
a surgical drape to cover and substantially conform to said basin to serve as a drape container for said liquid; and
sensing means for sensing conditions within said drape container, wherein said sensing means includes a plurality of conducting means for maintaining a potential, wherein said plurality of conducting means are disposed on a sterile drape surface within said drape container and extend to a non-sterile drape surface, and wherein said potentials of said plurality of conducting means are responsive to contact between said plurality of conducting means and said liquid and indicate conditions of said drape container, and wherein each of said drape container conditions corresponds to a different conducting means potential and said drape container conditions include presence of a leak within said drape container.

43. The detecting device of claim 42 wherein said drape includes an opening defined therein to permit passage of said plurality of conducting means therethrough and sealing means attached to a drape surface coincident said opening for sealing said opening and securing said plurality of conducting means within said drape container.

44. The detecting device of claim 42 wherein said drape includes securing means attached to said sterile drape surface for containing a proximal portion of each said conducting means, wherein said securing means includes a series of openings defined therein to enable said liquid within said drape container to contact said plurality of conducting means contained within said securing means.

45. The detecting device of claim 42 wherein said sensing means includes connecting means for receiving a distal end of each said conducting means and coupling said sensing means to said thermal treatment system.

46. The detecting device of claim 42 wherein:
    said thermal treatment system includes a plurality of said basins to thermally treat said liquid; and
    said drape covers and substantially conforms to each said basin to serve as said drape container for said liquid in each said basin, wherein said drape further includes a plurality of said sensing means each including a plurality of said conducting means disposed on said sterile drape surface within a corresponding drape container and extending therefrom to said non-sterile drape surface, and wherein potentials of said plurality of conducting means associated with a drape container are responsive to contact between those conducting means and said liquid and indicate conditions of that drape container.

47. The system of claim 1 wherein each of said plurality of conductors is disposed through said drape to extend between said sterile and non-sterile drape surfaces.

48. The system of claim 1 wherein said plurality of conductors each extend along said sterile drape surface and traverse a drape peripheral edge to extend between said sterile and non-sterile drape surfaces.

49. The system of claim 1 wherein said drape container conditions further include the presence and absence of said liquid within said drape container.

50. The device of claim 15 wherein each of said plurality of conductors is disposed through said drape to extend between said sterile and non-sterile drape surfaces.

51. The device of claim 15 wherein said plurality of conductors each extend along said sterile drape surface and traverse a drape peripheral edge to extend between said sterile and non-sterile drape surfaces.

52. The device of claim 15 wherein said drape container conditions further include the presence and absence of said liquid within said drape container.

53. The method of claim 21 wherein step (c) further includes:
    (c.1) determining occurrence of said drape container conditions from said potentials of said conductors, wherein said drape container conditions further include the presence and absence of said liquid within said drape container.

54. The method of claim 31 wherein step (b) further includes:
    (b.1) disposing said conductors through said drape to extend between said sterile and non-sterile drape surfaces.

55. The method of claim 31 wherein step (b) further includes:
    (b.1) disposing said conductors on said sterile drape surface to extend along that surface and traverse a drape peripheral edge to extend between said sterile and non-sterile drape surfaces.

56. The method of claim 31 wherein step (b) further includes:
    (b.1) disposing said conductors on said sterile drape surface within said drape container, wherein said potentials of said conductors indicate conditions of said drape container, and wherein said drape container conditions include the presence and absence of said liquid within said drape container.

57. The system of claim 37 wherein each of said plurality of conducting means is disposed through said drape to extend between said sterile and non-sterile drape surfaces.

58. The system of claim 37 wherein said plurality of conducting means extends along said sterile drape surface and traverses a drape peripheral edge to extend between said sterile and non-sterile drape surfaces.

59. The system of claim 37 wherein said drape container conditions further include the presence and absence of said liquid within said drape container.

60. The device of claim 42 wherein each of said plurality of conducting means is disposed through said drape to extend between said sterile and non-sterile drape surfaces.

61. The device of claim 42 wherein said plurality of conducting means extends along said sterile drape surface and traverses a drape peripheral edge to extend between said sterile and non-sterile drape surfaces.

62. The device of claim 42 wherein said drape container conditions further include the presence and absence of said liquid within said drape container.

63. The system of claim 1, wherein said surgical drape includes a pre-formed container portion configured to conform to said basin and serve as said drape container.

64. The device of claim 15, wherein said surgical drape includes a pre-formed container portion configured to conform to said basin and serve as said drape container.

65. The method of claim 21, wherein said surgical drape includes a pre-formed container portion configured to conform to said basin and serve as said drape container, and step (a) further includes:
    (a.1) placing said surgical drape over said thermal treatment system with said pre-formed container portion disposed in said basin to serve as said drape container.

66. The method of claim 31, wherein step (a) further includes:
    (a.1) forming said surgical drape to include a pre-formed container portion configured to conform to said basin and serve as said drape container.

67. The system of claim 37, wherein said surgical drape includes a pre-formed container portion configured to conform to said basin and serve as said drape container.

68. The device of claim 42, wherein said surgical drape includes a pre-formed container portion configured to conform to said basin and serve as said drape container.

* * * * *